(12) United States Patent
Kolli et al.

(10) Patent No.: US 12,109,091 B1
(45) Date of Patent: Oct. 8, 2024

(54) CRYPTOGRAPHICALLY SECURED DENTAL TREATMENT PLANNING

(71) Applicant: Align Technology, Inc., San Jose, CA (US)

(72) Inventors: Sreelakshmi Kolli, Fremont, CA (US); Leon Rasovsky, Mountain View, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 18/199,867

(22) Filed: May 19, 2023

Related U.S. Application Data

(63) Continuation of application No. 17/750,184, filed on May 20, 2022, now Pat. No. 11,742,065, which is a
(Continued)

(51) Int. Cl.
| | |
|---|---|
| *A61C 9/00* | (2006.01) |
| *A61C 7/00* | (2006.01) |
| *A61C 7/08* | (2006.01) |
| *B33Y 80/00* | (2015.01) |
| *G16H 10/60* | (2018.01) |

(Continued)

(52) U.S. Cl.
CPC ............ *A61C 9/0053* (2013.01); *A61C 7/002* (2013.01); *A61C 7/08* (2013.01); *B33Y 80/00* (2014.12); *G16H 10/60* (2018.01); *G16H 20/40* (2018.01); *H04L 9/3247* (2013.01); *A61C 2007/004* (2013.01)

(58) Field of Classification Search
CPC ......... A61C 9/0053; A61C 7/002; A61C 7/08; B33Y 80/00; G16H 20/40; G16H 10/60; H04L 9/3247
See application file for complete search history.

(56) References Cited

U.S. PATENT DOCUMENTS

| | | | | |
|---|---|---|---|---|
| 7,904,307 B2 * | 3/2011 | Abolfathi | ............... | G16H 50/50 600/300 |
| 8,024,198 B2 * | 9/2011 | Kuo | ....................... | G06Q 10/10 705/2 |

(Continued)

*Primary Examiner* — Nicholas D Lucchesi
(74) *Attorney, Agent, or Firm* — Lowenstein Sandler LLP

(57) ABSTRACT

A method of cryptographically secured digital dental treatment planning comprises: receiving, at an intraoral scanning system, an intraoral scan of a patient's dentition, wherein the intraoral scan comprises a three-dimensional (3D) surface representing the patient's dentition at a first arrangement; encrypting, at the intraoral scanning system, the intraoral scan to create a cryptographically secured dental record of the patient's dentition; decrypting, at a treatment planning system, the cryptographically secured dental record; determining a target arrangement for the patient's dentition; determining a digital treatment plan for the patient's dentition, wherein the digital treatment plan comprises a series of intermediate arrangements for a series of aligners to move the patient's dentition from the first arrangement toward the target arrangement; adding the digital treatment plan to the cryptographically secured dental record of the patient's dentition; and sending the cryptographically secured dental record of the patient's dentition to one or more data stores.

20 Claims, 14 Drawing Sheets

Related U.S. Application Data continuation of application No. 16/676,194, filed on Nov. 6, 2019, now Pat. No. 11,721,417.

(60) Provisional application No. 62/756,804, filed on Nov. 7, 2018.

(51) Int. Cl.
*G16H 20/40* (2018.01)
*H04L 9/32* (2006.01)

(56) References Cited

U.S. PATENT DOCUMENTS

| | | | |
|---|---|---|---|
| 8,075,306 B2 * | 12/2011 | Kitching | G16Z 99/00 |
| | | | 382/128 |
| 10,595,966 B2 * | 3/2020 | Carrier, Jr. | H04N 23/56 |
| 10,937,160 B1 * | 3/2021 | Ricci | G06Q 30/0631 |
| 11,327,943 B2 | 5/2022 | Lee | |
| 11,523,882 B2 * | 12/2022 | Shannon | A61C 7/14 |
| 11,721,417 B2 | 8/2023 | Rasovsky et al. | |
| 2002/0188478 A1 * | 12/2002 | Breeland | G06Q 30/06 |
| | | | 705/3 |
| 2008/0288289 A1 * | 11/2008 | Sah | A61C 7/00 |
| | | | 433/229 |
| 2019/0213333 A1 * | 7/2019 | Williams | H04L 9/3247 |
| 2020/0066391 A1 * | 2/2020 | Sachdeva | A61C 7/08 |
| 2020/0160947 A1 * | 5/2020 | Rasovsky | G16H 10/60 |
| 2020/0290262 A1 * | 9/2020 | Aguilar Mendez | B29C 51/46 |
| 2021/0236250 A1 * | 8/2021 | Braykovich | A61C 13/0019 |
| 2023/0088051 A1 * | 3/2023 | Corey | A61C 7/14 |

* cited by examiner

1250

Apply a first orthodontic appliance to a patient's teeth to reposition the teeth from a first tooth arrangement to a second tooth arrangement 1260

Apply a second orthodontic appliance to the patient's teeth to reposition the teeth from the second tooth arrangement to a third tooth arrangement 1270

FIG. 12

CRYPTOGRAPHICALLY SECURED DENTAL TREATMENT PLANNING

RELATED APPLICATIONS

The present application is a continuation of U.S. patent application Ser. No. 17/750,184, filed May 20, 2022, which is a continuation of U.S. patent application Ser. No. 16/676,194, filed Nov. 6, 2019, now U.S. Pat. No. 11,721,417, issued on Aug. 8, 2023

TECHNICAL FIELD

The present disclosure is generally related to handling electronic digital representations of patient anatomy by distributed computer systems and, in particular, to systems and methods implementing multi-dimensional cryptographically-secured datastores for managing medical records.

BACKGROUND

Medical treatment may involve evaluation of a medical condition, development and/or implementation of a treatment plan, coordination of medical resources, communication of healthcare needs to various stakeholders (patients, next of kin, healthcare providers, insurance entities, etc.), and/or evaluation of treatment results.

Medical treatment may be related to one or more treatment contexts, non-limiting examples of which include dental treatment (e.g., prosthodontic or orthodontic treatment); orthopedic treatment for bone, spinal, etc. conditions (e.g., osteoporosis); treatment for hearing, ear infections, and/or other ear conditions; dialysis and/or other procedures for treatment of kidney disease and/or malfunction; etc.

Medical treatment plans may use a variety of techniques. As an illustrative example, a prosthodontic treatment plan may call for manufacture, installation, and use of dental prosthesis on a dental site in a patient's oral cavity to treat gum disease, sleep apnea, and/or other intraoral conditions. An orthodontic treatment plan may use brackets and wires, retainers, clear aligners, and/or functional appliances to treat malocclusions and/or correct misalignment of a patient's dentition. In an illustrative example, an orthodontic treatment may be designed to move a patient's teeth to positions where function and/or aesthetics are optimized. Traditionally, appliances such as braces are applied to a patient's teeth by an orthodontist or dentist and the set of braces exerts continual force on the teeth and gradually urges them toward their intended positions. Over time and with a series of clinical visits and adjustments to the braces, the orthodontist adjusts the appliances to move the teeth toward their final destination. Alternatives to conventional orthodontic treatment with traditional affixed appliances (e.g., braces) include systems including a series of aligners. In these systems, multiple, and sometimes all, of the aligners to be worn by a patient may be designed and/or fabricated before the aligners are administered to a patient and/or reposition the patient's teeth (e.g., at the outset of treatment). The design and/or planning of a customized treatment for a patient may make use of computer-based three-dimensional (3D) planning/design tools. The design of the aligners can rely on computer modeling of a series of planned successive tooth arrangements, and the individual aligners are designed to be worn over the teeth and elastically reposition the teeth to each of the planned tooth arrangements.

As additional examples of medical treatment plans, orthopedic treatment plans may use surgical, interventional, minimally invasive, etc. procedures and/or medical devices to correct acute, degenerative, or other osteoporotic conditions. Other treatment plans may call for monitoring of medical conditions, corrective and/or other surgeries, application of medical devices (e.g., dialysis machines to perform kidney dialysis), and intervention (periodic or otherwise) by medical professionals.

A lot of digital data can be generated during the course of a medical treatment plan. Many dental treatment plans, for instance, call for a patient's dentition to be scanned at various points in time, including during initial/intermediate/final check-ups and/or at periodic intervals. These scans may include scans from an intraoral scanner or a digital representation of physical impressions captured at a treatment location. Three-dimensional (3D) representations and/or two-dimensional (2D) images of a patient's smile, face, dental arches, etc. may be developed/taken before, during and/or after dental treatment. These representations/images may show treatment progress for the patient, for example. Dental, orthopedic, nephritic, aural, and/or other treatment plans may generate video, images, anatomical renderings, notes, metadata, and other forms of digital data through the course of treatment.

While it would be desirable to manage digital data related to a medical treatment plan, existing systems do not always make it efficient or convenient to do so. For instance, many existing data management systems are insufficiently secure, and/or are insufficiently accessible by patients, healthcare providers, insurers, and/or other stakeholders. Many existing systems do not make it sufficiently convenient to leverage the digital data generated during a medical treatment plan into a variety of platforms, including but not limited to those used for: diagnostics, progress tracking, claims verification with insurers and/or other arbitrage entities, and supply chain management.

BRIEF DESCRIPTION OF THE DRAWINGS

The present disclosure is illustrated by way of example, and not by way of limitation, in the figures of the accompanying drawings.

FIG. 12 illustrates a method of orthodontic treatment using a plurality of appliances, in accordance with embodiments.

DETAILED DESCRIPTION

Figure 1:
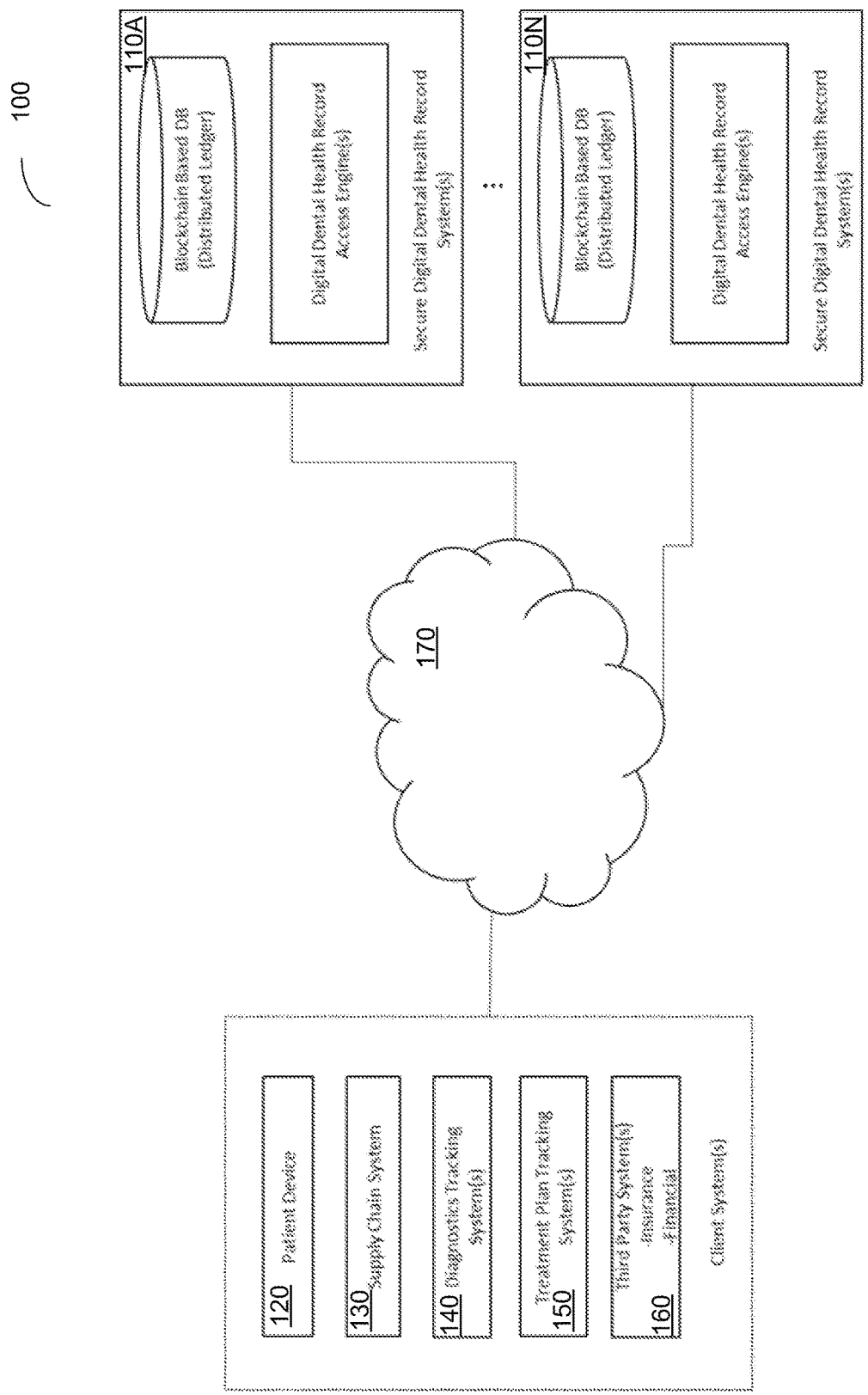
FIG. 1 schematically illustrates a high-level component diagram of an example distributed medical record management system implemented in accordance with one or more aspects of the present disclosure.

Discussed herein are systems and methods implementing multi-dimensional blockchain structures for storing digital representations of medical anatomy, such as digital representations of dental anatomy. The systems and methods herein address fundamental technical problems related to managing digital data that is generated and/or managed during the course of a medical treatment plan. The systems and methods herein use multi-dimensional blockchains to store the digital representations of medical anatomy that are generated during the course of a medical treatment plan. As noted herein, the systems and methods described herein allow various platforms (including those platforms related to diagnostics, progress tracking, claims verification with insurers and/or other arbitrage entities, and supply chain management) to leverage digital representations of medical anatomy.

A "blockchain," as used herein, may include a datastore of records (e.g., "blocks") that are linked to one another using cryptography. In some implementations, blocks of a blockchain may contain a cryptographic value (e.g., a cryptographic hash) of another block (e.g., of a previous block). Each block may contain other information, such as timestamps or other identifying information, and transaction data. Transaction data may be represented in a variety of formats, including as a hash (e.g., a merkle tree root hash). A blockchain may form a "distributed ledger" (e.g., a consensus of replicated, shared, and synchronized digital data geographically spread across multiple sites, countries, or institutions) that can record transactions between parties in a verifiable and/or permanent way. In some implementations, the blockchains herein may be managed by a network (e.g., a peer-to-peer (P2P) network) that collectively adheres to a protocol for inter-node communication and/or validation of new blocks. Once recorded, the data in a block in a blockchain may be protected from retroactive alteration without alteration of subsequent blocks (which may require consensus of the network).

A "digital representation of medical anatomy," (used interchangeably with "digital medical anatomy" and an "integrated medical record"), as used herein, may include a digital depiction or plurality of digital depictions of a patient's body and/or anatomy. A digital representation of medical anatomy, for instance, may include textual content (e.g., physician notes, referrals, test procedure results, prescriptions, orders, etc.) and multimedia content (e.g., audio files, video files, and/or medical images, such as electrocardiograms, three-dimensional (3D) scans, etc.). A digital representation of medical anatomy may include multimedia content items of medical records that is utilized in various medical fields. For example, in cardiology, electrocardiogram images or magnetic resonance images (MRI) may be utilized for diagnostics; in orthopedics, computer tomography (CT) and/or MRI images may be utilized for tracking the spine deterioration or the bone density; in nuclear medicine, CT and/or MRI images may be utilized for diagnosis and monitoring of cancerous tumors; in dentistry and/or orthodontics, digital representations of dental anatomy, such as three-dimensional (3D) intraoral scans or cone beam computer tomography (CBCT) images, may be utilized for planning implant surgery, designing tooth repositioning appliances, and/or various other applications.

A digital representation of medical anatomy may include an integrated online patient record. It may further include meta data (like traditional patient chart components such as progress notes, reports, medications, and orders) with multimedia patient data such as medical images, electrocardiograms, 3D scans, motion video and audio files. A digital representation of medical anatomy may include references (hyperlinks, pointers, etc.) to multimedia that is not stored in the patient's chart due to size or format limitations.

In the dental context, a digital representation of medical anatomy may include a digital representation of dental anatomy. A "digital representation of dental anatomy" used interchangeably with "digital dental anatomy," as used herein, may include a digital depiction or a plurality of digital depictions of a patient's dentition. Examples of digital representation(s) of dental anatomy include: the depictions (images and/or renditions) from an intraoral scanner, a digital depiction of the results of a physical mold used to capture a patient's dentition, a digital depiction of the results of a physical mold used to form an intraoral appliance, a three-dimensional (3D) image and/or rendering of a patient's dentition, etc. A digital representation of dental anatomy may include textual content (e.g., physician notes, referrals, test procedure results, prescriptions, etc.) and multimedia content (e.g., medical images, audio files, video files, etc.).

Digital representations of dental anatomy may be efficiently utilized, e.g., in orthodontics, dentistry (including restorative and cosmetic dentistry), prosthodontics, periodontics, or oral surgery. A digital representation of dental anatomy may include two-dimensional and/or three-dimensional images and/or depictions of a patient's dentition-acquired and/or utilized at various stage of treatment including design, manufacturing, fitting, and/or adjustment of orthodontic aligners.

Digital representations of dental anatomy may include intraoral images, which may be acquired using an intraoral scanner. These intraoral images may be used to generate three-dimensional virtual models of the patient's dental arch. At different stages of dental treatment (such as orthodontic treatment), additional 3D virtual models of the patient's dental arch may be generated. Virtual models may be used to model a patient's dentition through the course of a treatment plan. In some embodiments, virtual models, alone or in conjunction with one or more transformations, may be used to model orthodontic aligners (e.g., polymeric aligners) for various treatment stages of a treatment plan.

Virtual models may be used to model orthodontic aligners (e.g., polymeric aligners) for various treatment stages of a treatment plan. Various additional two-dimensional and/or three-dimensional images, such as images of a patient's smile, face, dental arches, etc. may be acquired before, during and/or after the treatment, in order to perform various tasks, such as provide a photographic simulation of an outcome of a proposed treatment plan, track progress of a treatment plan, determining efficacy of appliances (e.g., tooth repositioning appliances) used to implement the treatment plan, etc.

As another example, a digital representation of dental anatomy may include intraoral scans of a patient's dentition at various times, including at various times (before treatment, intermediate treatment stages, after a final treatment stage, etc.) through the course of a treatment plan. A digital representation of dental anatomy may include models of estimated results of application of a treatment plan (or portion thereof) on a patient's dentition, such as a 3D model and/or image of an estimated result of at least a portion of the treatment plan. A digital representation of dental anatomy may include multiple portions, such that each portion may reflect a specific medical event (such as a patient visit, a diagnostic procedure and/or treatment performed, etc.). Intraoral images of a patient dentition may be generated by using an intraoral scanner and/or camera. Intraoral images may be used to generate a three-dimensional virtual model of the patient's teeth and surrounding gingiva tissues. Various three-dimensional and/or two-dimensional representations of a patient's smile, face, dental arches, etc., may be acquired before, during and/or after the treatment.

Figure 10:
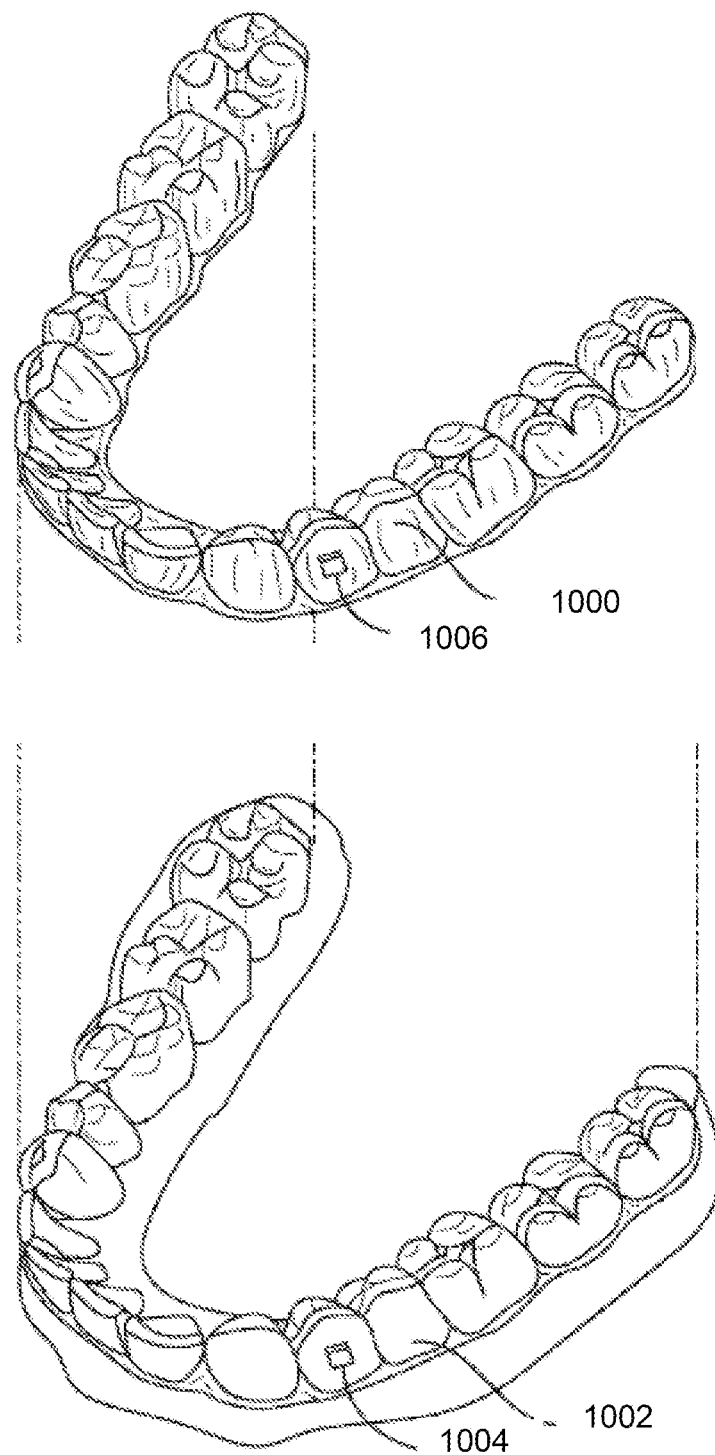
FIG. 10 illustrates a tooth repositioning appliance, in accordance with embodiments.
Figure 11:
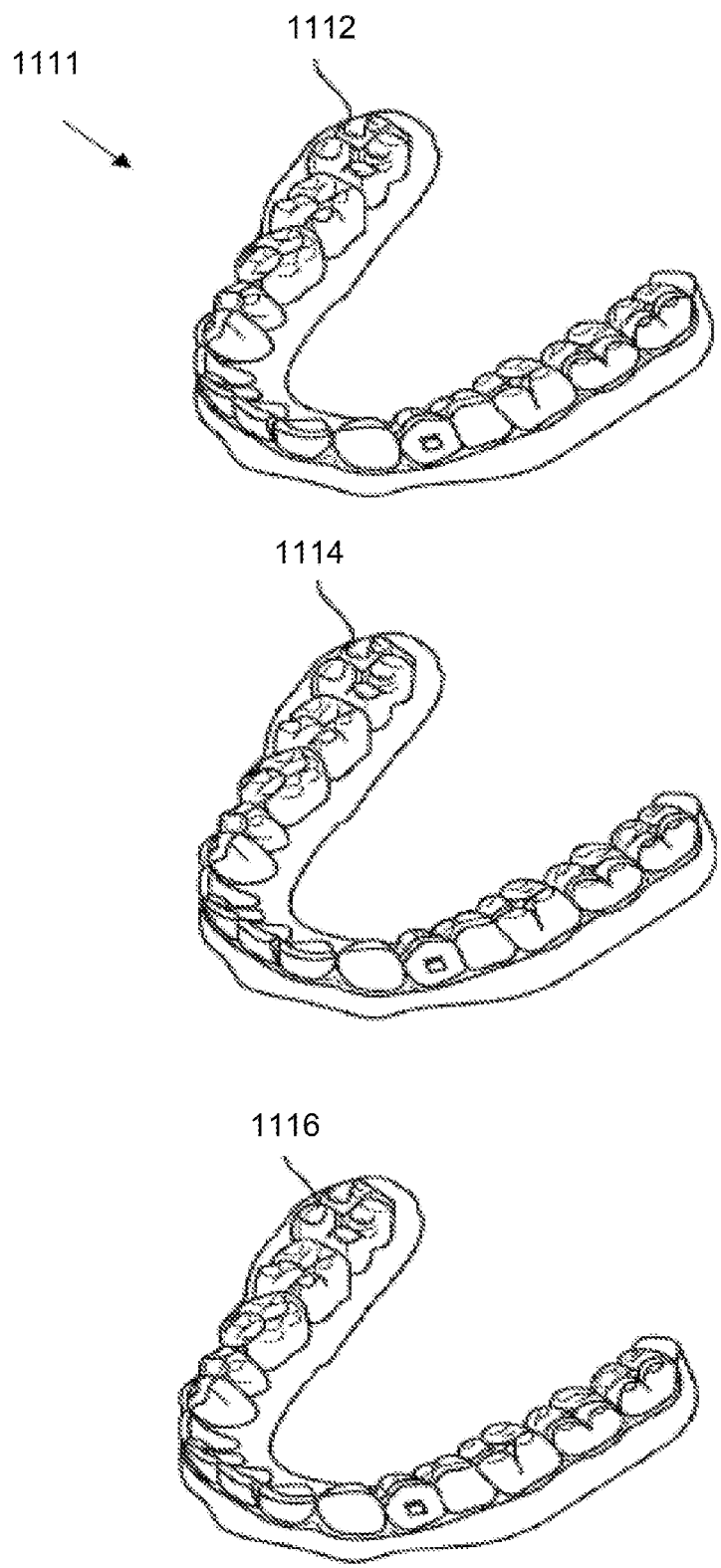
FIG. 11 illustrates a tooth repositioning system, in accordance with embodiments.

Tooth repositioning appliances (such as orthodontic aligners) and/or tooth repositioning systems (such as systems of orthodontic aligners) may be used to correct malocclusions to a patient's dentition. Examples of such tooth repositioning appliances/systems are shown in FIGS. 10 and 11. Tooth repositioning appliances may be used as part of an orthodontic treatment plan, an example of which is described in conjunction with FIG. 12. Many orthodontic treatment plans prescribe treatment by a series of orthodontic aligners, such that each orthodontic aligner of the series would implement a specific stage of a treatment plan, and/or has unique properties (e.g., shape(s)) compared to other orthodontic aligners in the series. Though the number of orthodontic aligners used to implement an orthodontic treatment plan may vary, many cases can prescribe from several to several dozen (e.g., 50-60) stages. Each stage may be implemented by an orthodontic aligner specifically configured, alone, or in combination with other structures (such as attachments) to implement force systems unique to that stage. Each stage may be modeled by a variety of techniques, including by intraoral and/or other images taken from an intraoral scanner, by a digital rendering of a physical mold of a patient's dentition, by modeling the estimated results of a treatment plan (or portion thereof) on the patient's dentition, by taking images of a patient's dentition with a camera or a phone, etc. Each stage may have one or more digital representations of dental anatomy associated with it.

In some implementations, digital representation(s) of dental anatomy may be stored in distributed databases implemented as blockchains, thus providing immutability, consistency, and availability of the digital representations of dental anatomy while avoiding common pitfalls of centralized or hierarchical solutions. In some implementations, the digital representation(s) of dental anatomy may be associated with specific medical event (such as a patient visit, a diagnostic procedure and/or treatment performed, etc.).

In an illustrative example, a digital representation of dental anatomy portion, which may include one or more data items (e.g., multiple data items related to a single patient visit), may be stored as a single transaction record in a blockchain.

A blockchain may implement an immutable (append-only) database in which replicas of each transaction record, grouped in transaction blocks, are stored by multiple nodes. The transaction records stored on the blockchain may be cryptographically protected, e.g., by digital signatures of the transaction initiating nodes. A consensus protocol may be implemented for the blockchain for validating transaction records by a majority of nodes, in order to enforce the transaction record immutability, thus making the blockchain an append-only data structure. In an illustrative example, the blockchain may implement a proof-of-work consensus protocol, which requires that a node, before broadcasting a block of transaction records, compute a value of a cryptographic nonce such that a certain hash function applied to the block would produce a pre-determined result. The significant computational complexity of this nonce computation operation makes it computationally infeasible for a majority of nodes to modify a previously issued transaction block. In various other illustrative examples, other consensus protocols may be employed by systems and methods described herein.

In order to address pertinent security and privacy requirements, systems and methods of the present disclosure may utilize private blockchains or permissioned public blockchains, and may further encrypt the digital representation of dental anatomy data using secret cryptographic keys, as described in more detail herein below.

As noted herein above, a digital representation of dental anatomy portion, which may include one or more data items (e.g., multiple data items related to a single patient visit), may be stored as a single transaction record in a blockchain. The size of a transaction block may be pre-determined according to requirements of a particular blockchain implementation. The block size would usually fall within the range between several kilobytes and several megabytes (for example, the Bitcoin network currently operates with 1 Mb blocks). The limited block size, which can be small in comparison to the size of a corresponding multimedia content file (e.g., a three-dimensional rendering/representation of a patient's dentition), may represent an impediment to utilizing blockchains for storing medical records which include such images and/or other multimedia content.

Systems and methods described herein may effectively address the block size limitation by storing the multimedia content of a digital representation of dental anatomy on an external storage (such as cloud-based storage or any other network-accessible storage) rather than on the blockchain itself. For instance, a blockchain could be employed for storing the textual content of a digital representation of dental anatomy and an identifier of the external storage location of the multimedia content of the digital representation of dental anatomy. This approach preserves immutability, consistency, and availability of medical records while relieving a blockchain from the burden of storing large multimedia content files.

While the examples described herein are related to storing multimedia content of digital representations of dental anatomy, the systems and methods of the present disclosure may similarly enable utilizing multi-dimensional blockchain structures for storing multimedia content for various other applications. In an illustrative example, the multimedia content may include digital models and/or images utilized for 3D printing. In another illustrative example, the multimedia content may include audiovisual content. In another illustrative example, the multimedia content may include digital models and/or images utilized for computer-aided design (CAD).

In some embodiments, it may be desirable to allow migration of multimedia content: the immutability of records stored in the blockchain inhibits modifications of the identifiers of the external storage locations referenced by the blockchain records, even if a particular multimedia content item has been migrated to another storage location. "Migration of multimedia content" herein shall refer to moving the multimedia content from a source external storage location to a destination external storage location, such that the two locations are addressable by different location identifiers (e.g., Universal Resource Identifiers (URIs)). In an illustrative example, such migration may be performed by transmitting the multimedia content over one or more networks from the source external storage location to the destination external storage location. Such migration may be caused by various reasons, e.g., data center consolidation, migration from a private data center to a public cloud, migration from one cloud service provider to another cloud service provider, etc.

In order to allow migration of the multimedia content, the systems and methods described herein employ a two-dimensional blockchain structure, in which the main blockchain is employed to store non-multimedia (e.g., textual) content of medical records while multiple auxiliary blockchains store identifiers of external storage locations utilized for storing the multimedia content of the digital representations of dental anatomy. Accordingly, a typical block of the main blockchain, in addition to storing non-multimedia portions of a digital representation of dental anatomy, could include a reference to an associated auxiliary blockchain which stores identifiers of external storage locations utilized for storing the multimedia content of the digital representations of dental anatomy, as described in more detail herein below. The terms "main blockchain" and "auxiliary blockchain" are used herein to designate two blockchains. It is noted the terms "main" and "auxiliary" may, but need not, impose a hierarchical or other relationship between the two types of blockchains.

The systems and methods described herein may be efficiently utilized for tracking a patient's progress according to a planned treatment, incorporating enhanced tracking techniques into the treatment delivery and management, and modifying the patient's treatment plan based on a determination that treatment has progressed off track. Information obtained according to the invention techniques can be used, for example, to more actively and/or effectively manage delivery of orthodontic treatment, increasing treatment efficacy and successful progression to the patient's teeth to the desired finished positions.

Various aspects of the above-referenced methods and systems are described in detail herein below by way of examples, rather than by way of limitation. While specific examples described herein are related to orthodontic treatments, the systems and methods of the present disclosure may similarly be employed by in dentistry (including prosthodontic (restorative and cosmetic) and orthodontic procedures), oral surgery, and/or various other medical areas in which two-dimensional images, three-dimensional images and/or other multimedia content of medical records may be utilized.

In various implementations of the systems and methods of the present disclosure, a distributed database for medical record management may be implemented as a blockchain, the nodes of which may be maintained by patient treatment facilities, health insurance providers, and/or other relevant parties, as schematically illustrated by FIG. 1. As shown in FIG. 1, the blockchain 100 may include multiple nodes 110A-110B which store copies of the digital representation of dental anatomy management database. Various client systems, such as patient devices (e.g., smartphones) 120, supply chain systems 130, diagnostic tracking systems 140, treatment plan tracking systems 150, and/or third party systems 160 (such as health insurance providers) may access the database through the network 170, which may include a combination of a wide area networks (such as the Internet) and local area networks.

Figure 2:
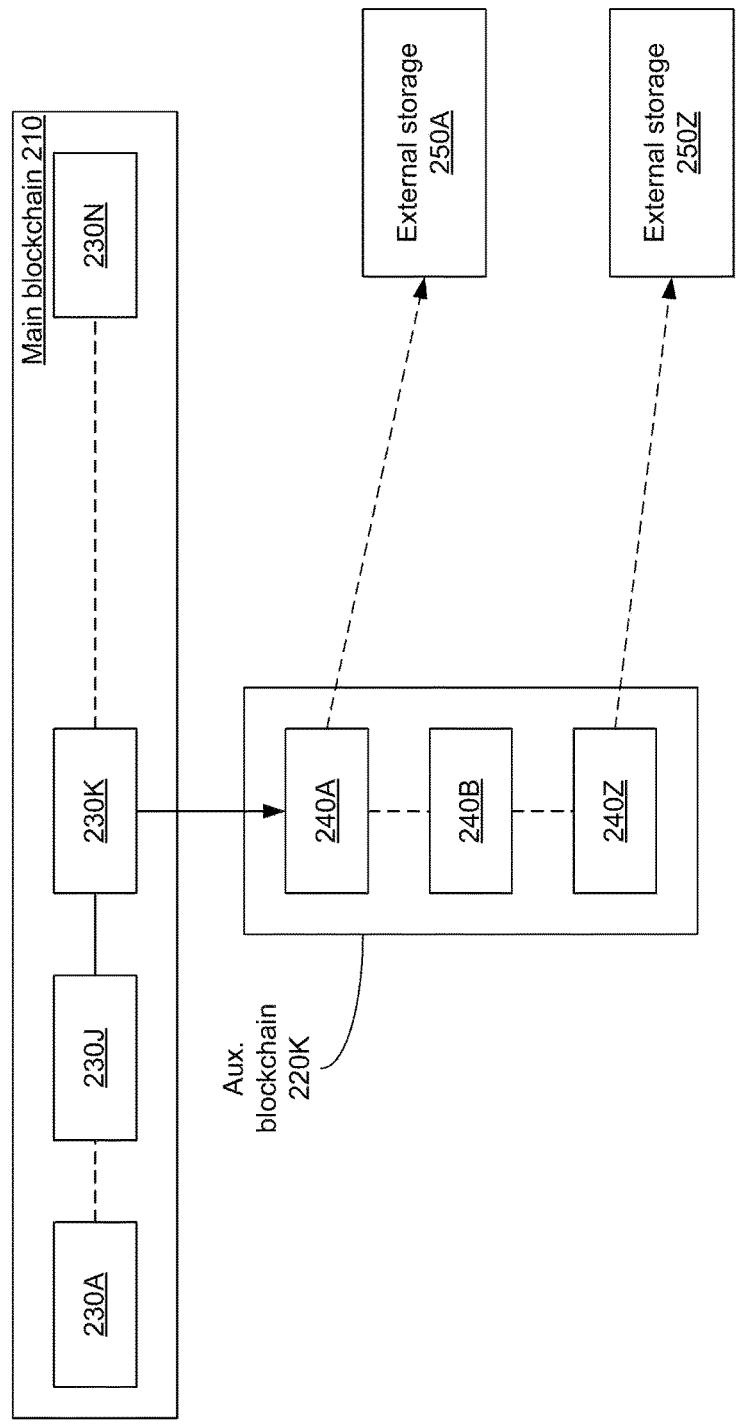
FIG. 2 schematically illustrates two-dimensional blockchain structures for storing medical records implemented in accordance with one or more aspects of the present disclosure.

FIG. 2 schematically illustrates an example two-dimensional blockchain structure 200 which may be utilized by systems and methods described herein. As shown in FIG. 2, the example blockchain structure 200 may include a main blockchain 210 and multiple auxiliary blockchains 220A-220N, such that each auxiliary blockchain 220 is referenced by a pointer stored by a respective block 230 of the main blockchain 220. The main blockchain 220 may include a sequence of blocks 230A-230N which may be employed for storing medical record data, except for the multimedia content. In an illustrative example, the sequence of blocks 230A-230N of the main blockchain 220 may store medical record data items in the chronological order, such that the most recent event would be reflected by the digital representation of dental anatomy data item stored by the most recently created block 230N of the main blockchain 220.

At least some of the blocks 230A-230N of the main blockchain may reference respective auxiliary blockchains 220A-220N. An auxiliary blockchain 220 including a sequence of blocks 240A-240Z may be employed for storing identifiers of the locations of the external storage 250A-250Z storing the associated multimedia content (e.g., medical images). In various illustrative examples, the external storage may be provided by a cloud-based storage or any other type of network-accessible storage. The external storage may implement various clustering, load balancing, and/or high availability features (e.g., quorum-based clustering with weighted round-robin load balancing).

Figure 3:
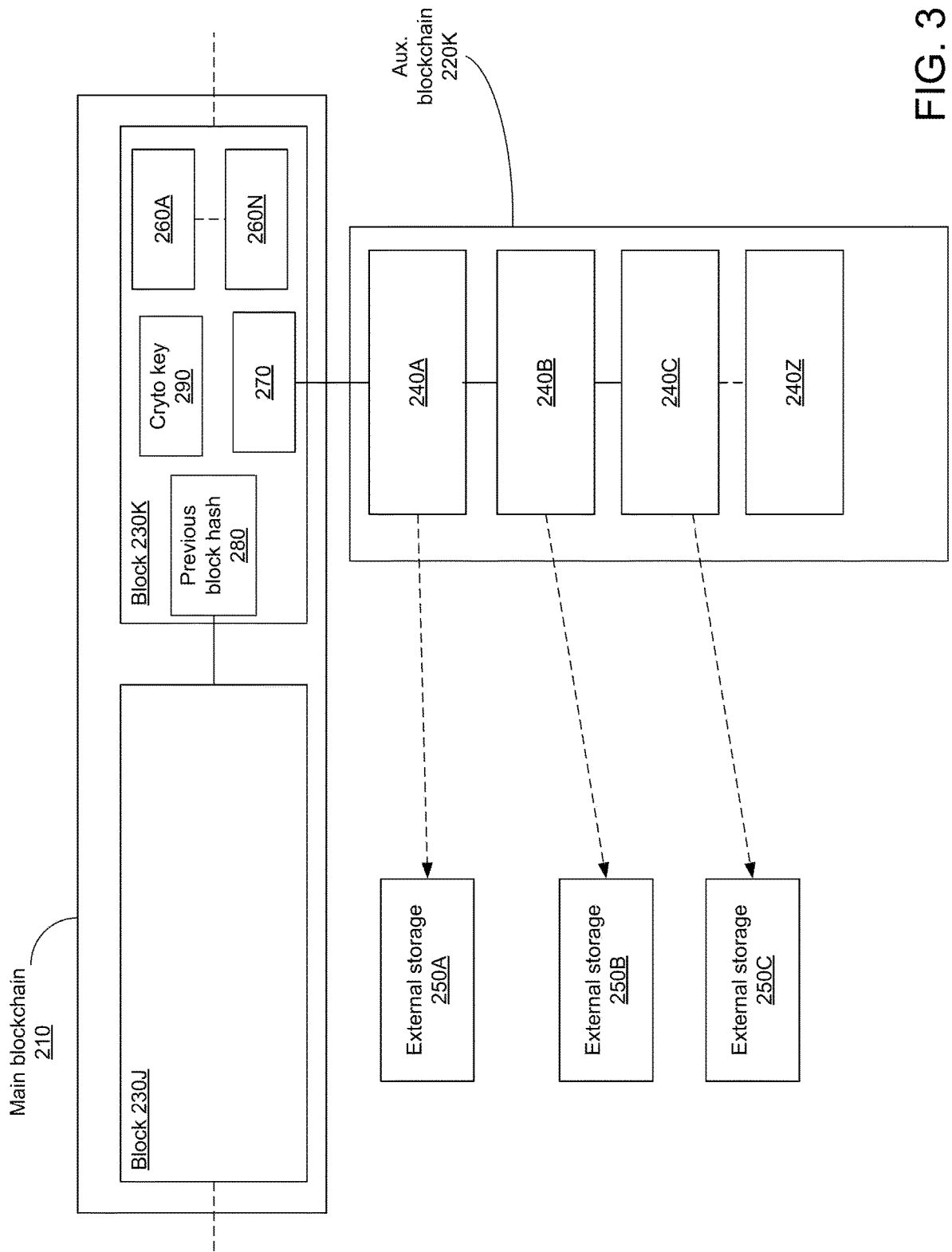
FIG. 3 schematically illustrates example block structures of the main and auxiliary blockchains implemented in accordance with one or more aspects of the present disclosure.

As schematically illustrated by FIG. 3, an example block 230K of the main blockchain 220 stores one or more medical record data items 260A-260N which are related to a single medical event (e.g., an outpatient visit to a patient treatment facility). The digital representation of dental anatomy data items 260A-260N may include various textual and/or numerical content (e.g., physician notes, referrals, test or procedure results, prescriptions, wearable device data, etc.). The example block 230K of the main blockchain 220 may further store a reference 270 (e.g., a pointer) to the leading block 240A of the associated auxiliary blockchain 220K. Blocks of the main blockchain 200 may further include various other fields, which are omitted from FIGS. 2-2 for clarity and conciseness.

As schematically illustrated by FIGS. 1-2, the auxiliary blockchain 220K referenced by the example block 230K of the main blockchain 210 may include one or more blocks 240A-240Z employed for storing identifiers of external storage locations storing the multimedia content associated with the block 230K of the main blockchain 210. Thus, when a new block (e.g., the example block 230K) of the main blockchain 210 is created for storing one or more medical record data items 260A-260N, the associated multimedia content (e.g., one or more medical images) is stored in an external storage location 250A. An identifier of the external storage location 250A (e.g., in the form of Universal Resource Identifier (URL)) is stored in a newly created block 240A of the auxiliary blockchain 220K. Finally, a reference 270 (e.g., a pointer) to the block 240A of the auxiliary blockchain 220L is stored in the block 230K of the main blockchain 220.

In order to enforce blockchain immutability, each block of the main blockchain 220, including the example block 230K, may include a cryptographic hash 280 of the previous block (e.g., the block 230J) of the main blockchain 220. Storing, in each block of the main blockchain 220, a cryptographic hash of the previous block, in combination with other cryptographic protection features, make the blockchain immutable, as described in more detail herein below with references to FIG. 5.

In various implementations of the systems and methods described herein, the multimedia content stored in the external storage may be cryptographically encrypted in order to address pertinent security and privacy concerns and/or regulations. In an illustrative example, referring again to FIG. 2, a secret cryptographic key 190 utilized for cryptographically encrypting the multimedia content before storing the multimedia content in the external storage may be stored by the associated block 230 of the main blockchain 220. In another illustrative example, the secret cryptographic key utilized for cryptographically encrypting the multimedia content may be stored by the associated block 240 of the auxiliary blockchain 220.

Referring to FIG. 2, if the multimedia content that has been initially stored in the external storage location 250A is later migrated to a new external storage location 250B (which, in an illustrative example, may be within the same or different private cloud or public cloud as the storage location 250A), a new block 240B of the auxiliary blockchain 220K is created. An identifier of the external storage location 250B (e.g., in the form of URL) is stored in the newly created block 240B of the auxiliary blockchain 220.

Similarly, as schematically illustrated by FIG. 3, if the multimedia content that has been stored in the external storage location 250B is later migrated to a new external storage location 250C (which, in an illustrative example, may be within the same or different private cloud or public cloud as the storage locations 250A and/or 250C), a new block 240C of the auxiliary blockchain 220K is created. An identifier of the external storage location 250C (e.g., in the form of URL) is stored in the newly created block 240C of the auxiliary blockchain 220K. Blocks of the auxiliary blockchain 220K may further include various other fields, which are not shown in FIG. 3.

Referring again to FIG. 2, retrieval of a specified medical record portion (e.g., a digital representation of dental anatomy portion identified by a specified patient identifier and a date) may involve identifying, in the main blockchain 210, the block (e.g., the example block 230K) which stores the requisite medical record portion. In an illustrative example, identifying the relevant block 230K may involve traversing the main blockchain 210 starting from the initial block until the relevant block is found (e.g., the block storing the requisite medical record portion identified by the specified patient identifier and the date). In another illustrative example, search for the relevant block may be facilitated by an index associated with the main blockchain 210, such that each index entry would map, for a given patient, a date (such as a date of outpatient visit to a patient treatment facility) to an identifier of a block of the main blockchain 210 which stores the digital representation of dental anatomy portion pertinent to the specified date.

Responsive to determining that the identified block 230K includes a valid reference to the leading block 240A of the corresponding auxiliary blockchain 220K, the computer system implementing the digital representation of dental anatomy retrieval operation may traverse the auxiliary blockchain 220L starting from the initial block 240A. Traversal of the auxiliary blockchain may be performed until the terminal block 240Z is found, such that the auxiliary blockchain 220K contains no blocks following the identified terminal block 240Z. As explained herein above, the terminal block 240Z of the auxiliary blockchain 220L would store the identifier (e.g., in the form of URL) of the external storage location 250Z of the multimedia content (e.g., one or more medical images) associated with the digital representation of dental anatomy portion stored by the block 230K of the main blockchain 210.

Accordingly, in operation, newly created records may be broadcasted by the initiator node (e.g., a patient treatment facility) and may be received by all currently active blockchain nodes. Each transaction record may be digitally signed by the initiator's private key, such that other nodes would be able to validate the digital signature using the public key of the transaction initiator node.

Figure 4:
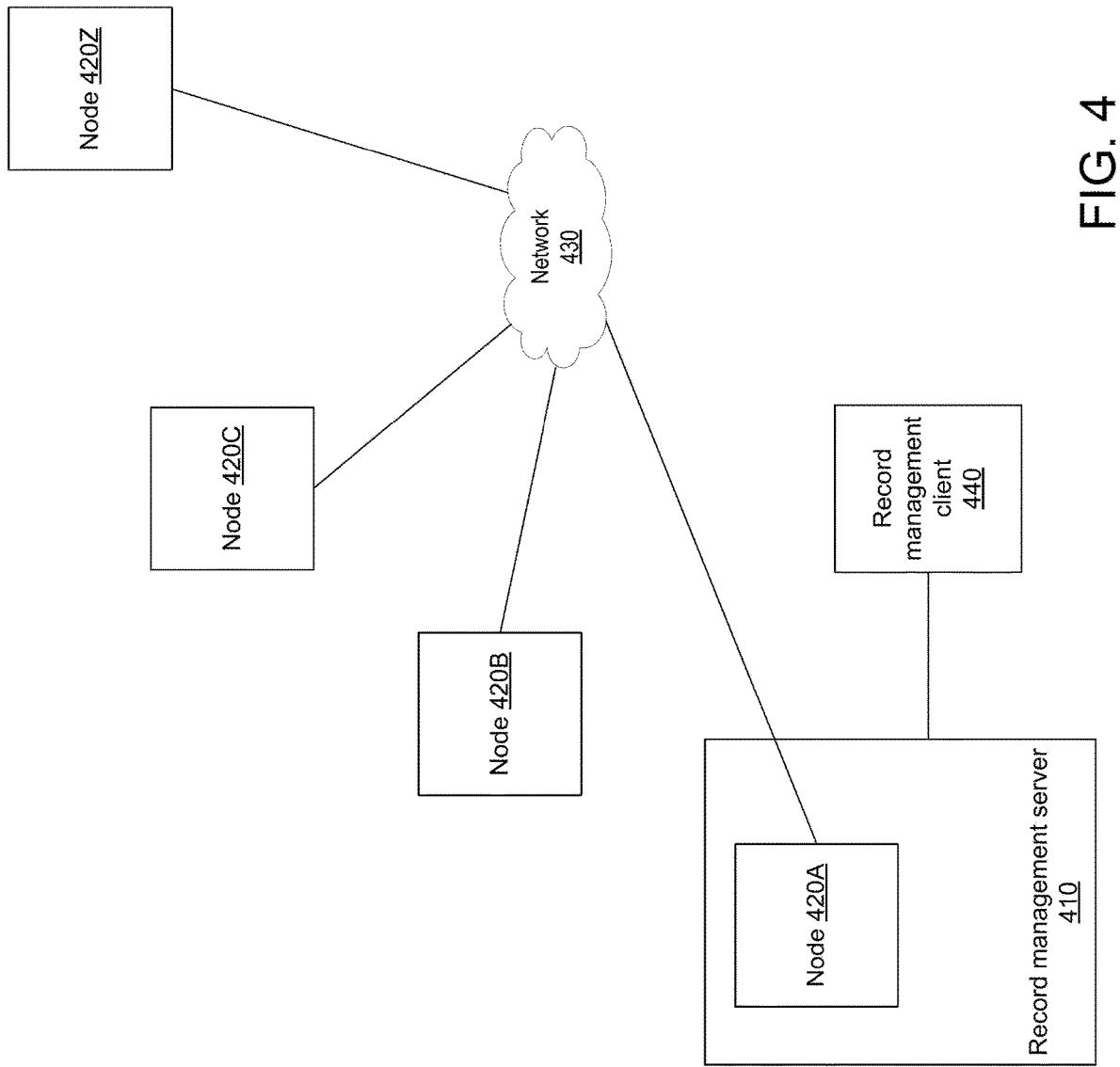
FIG. 4 schematically illustrates a high-level component diagram of another example distributed medical record management system implemented in accordance with one or more aspects of the present disclosure.

In various implementations of the systems and methods of the present disclosure, nodes of the main blockchain may be maintained by patient treatment facilities, health insurance providers, and/or other relevant parties. As schematically illustrated by FIG. 4, a patient treatment facility may have a digital representation of dental anatomy management system, which may include a digital representation of dental anatomy management server 410 implementing functions of a blockchain node 420A of the main blockchain including multiple nodes 420A-420Z communicating to each other via a network 430. In course of an outpatient visit to a patient treatment facility, a three-dimensional intraoral image of the patient may be acquired. The patient treatment facility staff may employ a digital representation of dental anatomy management client 440 (e.g., a personal computer, a tablet, or a similar computing device) to cause the digital representation of dental anatomy management server 410 to create, in the main blockchain, a new block for storing the digital representation of dental anatomy portion associated with the outpatient visit. The digital representation of dental anatomy management server 410 may encrypt the newly acquired three-dimensional intraoral image using a secret cryptographic key, and may store the newly acquired image in an external storage location (e.g., a cloud-based storage location). The digital representation of dental anatomy management server 410 may then create a new auxiliary blockchain block for storing an identifier of the external storage location, as described in more detail herein above with references to FIGS. 2-3.

In course of a subsequent patient visit to the patient treatment facility, the patient treatment facility staff may employ a digital representation of dental anatomy management client 440 (e.g., a personal computer, a tablet, or a similar computing device) to cause the digital representation of dental anatomy management server 410 to retrieve the previously saved image and display the image on the screen of the digital representation of dental anatomy management client 440. Furthermore, in course of a subsequent patient visit to the patient treatment facility, a new three-dimensional intraoral image may be acquired, and a corresponding record may be appended to the main blockchain, as described in more detail herein above with references to FIGS. 2-3.

In order to address pertinent security and privacy requirements, systems and methods of the present disclosure may utilize private blockchains or permissioned public blockchains. A private or permissioned blockchain may be implemented by establishing access control procedures with respect to the blockchain nodes, such that only authenticated and authorized nodes would be able to receive the new block broadcasts and/or access blockchain records stored by one or more servers implementing the nodes of the private blockchain. Furthermore, access control may be also implemented with respect to the public keys of the blockchain participants (which are needed to verify digital signatures of the data blocks).

Figure 5:
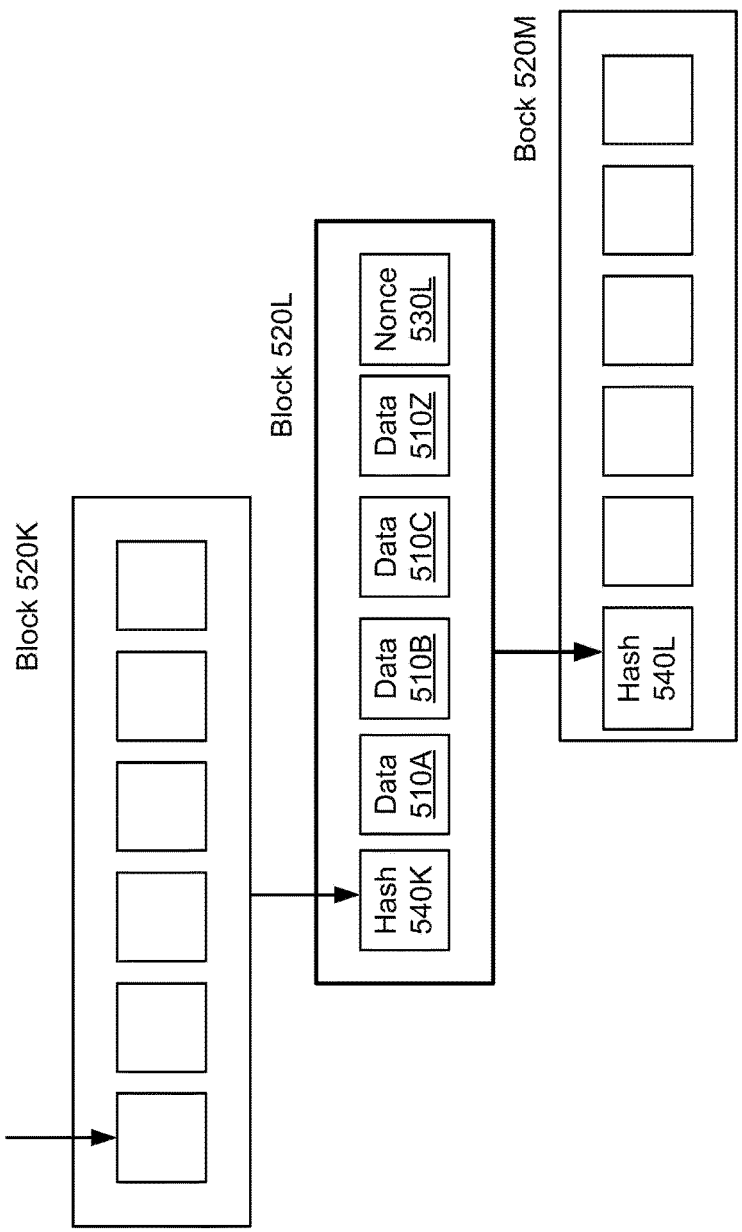
FIG. 5 schematically illustrates an example blockchain implementing a proof-of-work consensus protocol in accordance with one or more aspects of the present disclosure.

As noted herein above, a consensus protocol may be implemented for the blockchain for validating transaction records by a majority of nodes, in order to enforce the transaction record immutability, thus making the blockchain an append-only data structure. In an illustrative example, the blockchain may implement a proof-of-work consensus protocol, which requires that a node, before broadcasting a block of transaction records, compute a value of a cryptographic nonce such that a certain hash function applied to the block would produce a pre-determined result (e.g., a pre-determined binary value), as schematically illustrated by FIG. 5. The significant computational complexity of this nonce computation operation makes it computationally infeasible for a majority of nodes to modify a previously issued transaction block. In various other illustrative examples, other consensus protocols may be employed by systems and methods described herein.

In operation, a blockchain node may assemble several data items 510A-510Z into a block, and may perform one or more cryptographic operations on the block to produce a cryptographically protected block 520L. In order to enforce the blockchain immutability, each block of the blockchain, including the example block 520, includes a cryptographic hash 540K of the previous block (e.g., the block 520K) of the blockchain.

In an illustrative example, cryptographically protecting a block may involve incrementing a nonce field 530L comprised by the block until a value of the nonce is found such that a cryptographic hash 540L of the block would satisfy a pre-defined condition (e.g., comprise a pre-determined number of leading zero bits). A cryptographic hash may be represented by an irreversible function mapping a first bit sequence of arbitrary size to a second bit sequence of a pre-determined size, such that two different bit sequences are unlikely to produce the same hash value. The computations performed in order to cryptographically protect a block may be referred to as "proof-of-work." In various other illustrative examples, other consensus protocols (such as "proof-of-stake") may be employed by systems and methods described herein. In the "proof-of-stake" protocol, each block is validated by a blockchain participant who can demonstrate ownership of at least a part of a certain pool of assets. In various modifications of the "proof-of-stake" protocol, a validator's "stake" may be diminished in response to detecting a false validation (i.e., validation of an invalid block) performed by the validator.

Upon producing a cryptographically protected block 520L, the node may broadcast the cryptographically protected block 520L to the peer nodes and save the node in the local persistent storage (e.g., a database).

As noted herein above, the systems and methods described herein may be efficiently utilized for tracking a patient's progress according to a planned treatment, incorporating enhanced tracking techniques into the treatment delivery and management, and modifying the patient's treatment plan based on a determination that treatment has progressed off track. Information obtained according to the invention techniques can be used, for example, to more actively and/or effectively manage delivery of orthodontic treatment, increasing treatment efficacy and successful progression to the patient's teeth to the desired finished positions.

Thus, in one aspect, the systems and methods described herein may be employed for identifying deviations from a patient treatment plan, which may involve, for example, receiving a digital representation of an actual arrangement of a patient's teeth in course of implementing an orthodontic treatment plan and comparing the actual arrangement to a pre-determined planned arrangement to determine if the actual arrangement substantially deviates from the planned arrangement. Such comparison may involve determining one or more positional differences between the actual and planned arrangements of at least some of the corresponding teeth.

The systems and methods described herein may be further employed for managing delivery and patient progression through an orthodontic treatment plan, which may involve, for example, providing an initial treatment plan for a patient, providing a set of orthodontic appliances to the patient, tracking progression of the patient's teeth along the treatment path, comparing the actual arrangement with a planned arrangement to determine if the actual arrangement of the teeth matches a planned tooth arrangement, and generating a revised treatment plan where it is determined that the actual tooth arrangement deviates from the planned tooth arrangement. In another example, a method can include receiving a digital representation of an actual arrangement of a patient's teeth in course of implementing the orthodontic treatment plan; comparing the actual arrangement to a digital model of a planned arrangement, and generating a revised treatment plan. Additionally, as noted herein, the systems and methods herein may be used for diagnostics, claims verifications with an arbitrage entity, and/or supply chain management.

Figure 6:
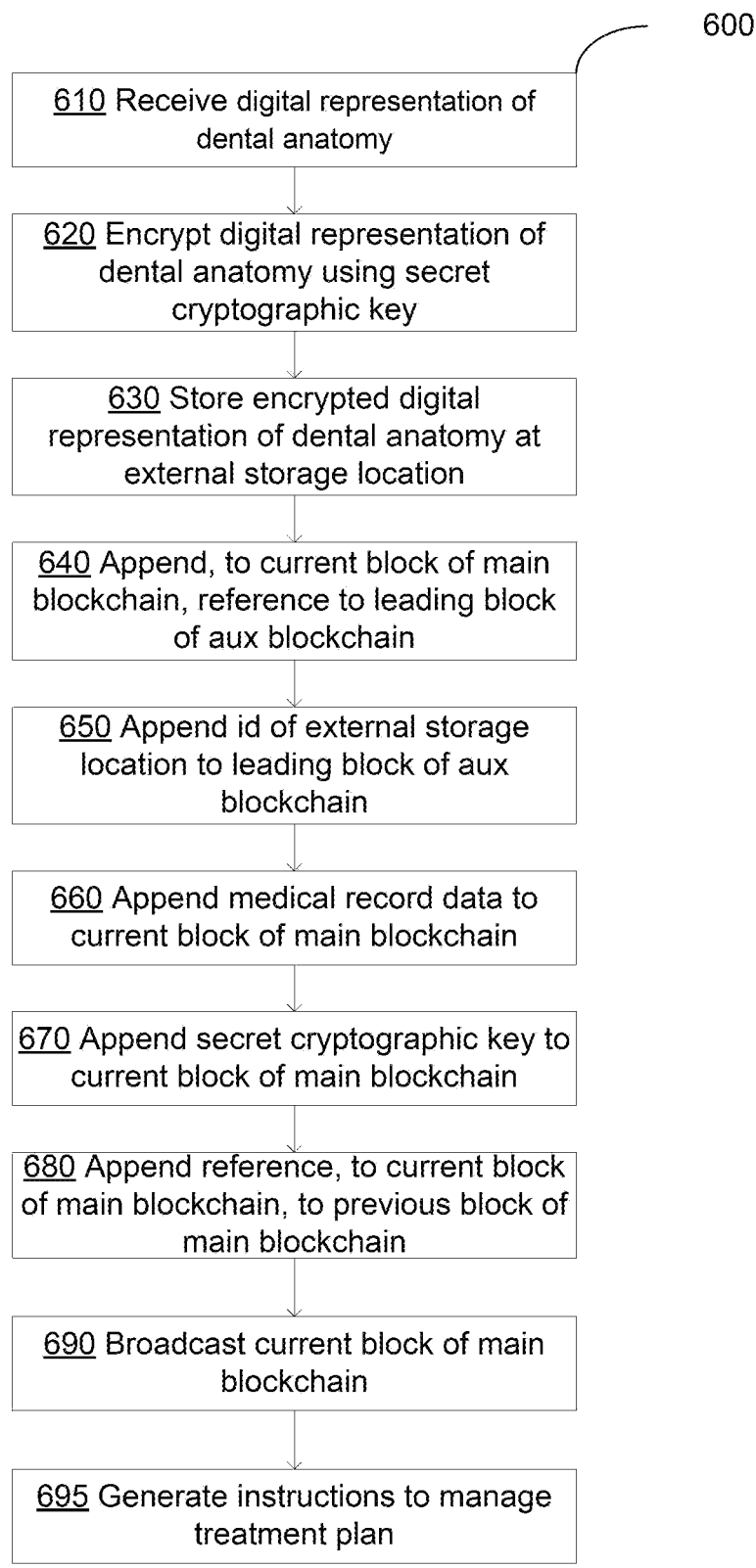
FIG. 6 depicts a flow diagram of one illustrative example of a method of storing digital representations of dental anatomy utilizing the two-dimensional blockchain structure implemented in accordance with one or more aspects of the present disclosure.

FIG. 6 depicts a flow diagram of one illustrative example of a method of storing digital representations of dental anatomy utilizing the two-dimensional blockchain structure implemented in accordance with one or more aspects of the present disclosure. Method 600 and/or each of its individual functions, routines, subroutines, or operations may be performed by one or more processors of the computer system (e.g., example computing device 900 of FIG. 9) executing the method. In various implementations, method 600 may be performed by a single processing thread. Alternatively, method 600 may be performed by two or more processing threads, each thread executing one or more individual functions, routines, subroutines, or operations of the method. In an illustrative example, the processing threads implementing method 600 may be synchronized (e.g., using semaphores, critical sections, and/or other thread synchronization mechanisms). Alternatively, the processing threads implementing method 600 may be executed asynchronously with respect to each other. Therefore, while FIG. 6 and the associated description lists the operations of method 600 in certain order, various implementations of the method may perform at least some of the described operations in parallel and/or in arbitrary selected orders.

At block 610, a computing device implementing the method may receive a digital representation of dental anatomy (e.g., by performing an intraoral scan of an oral cavity of a patient). In an illustrative example, the digital representation of dental anatomy may a three-dimensional intraoral representation of a patient's dentition, as described in more detail herein above.

At block 620, the computing device may encrypt the digital representation of dental anatomy using a secret cryptographic key, as described in more detail herein above. In an illustrative example, the secret cryptographic key may be generated by a software-implemented method applying a key-generation function to an entropy source (e.g., a random number generator). In another illustrative example, the secret cryptographic key may be generated by a hardware device, such as a hardware security module (HSM).

At block 630, the computing device may cause the encrypted digital representation of dental anatomy to be stored at an external storage location. In an illustrative example, the computing device may transmit the encrypted digital representation of dental anatomy to a cloud-based storage server, as described in more detail herein above.

At block 640, the computing device may append, to the current data block of the main blockchain utilized for storing the digital representations of dental anatomy, a reference to the leading data block of an auxiliary blockchain utilized for storing references to external storage locations of the digital representations of dental anatomy multimedia content.

At block 650, the computing device may append, to the leading data block of the auxiliary blockchain, an identifier of the external storage location (e.g., in the form of a URI) in which the digital representation of dental anatomy is stored.

At block 660, the computing device may append, to the current data block of the main blockchain, one or more data items of the digital representation of dental anatomy. The data items may be utilized for storing textual and/or numerical content associated with the digital representation of dental anatomy, which in various illustrative examples may include physician notes, referrals, test or procedure results, prescriptions, wearable device data, etc., as described in more detail herein above.

At block 670, the computing device may append, to the current data block of the main blockchain, a data item storing the secret cryptographic key utilized for encrypting the digital representation of dental anatomy, as described in more detail herein above.

At block 680, the computing device may append, to the current data block of the main blockchain, a reference to the preceding data block of the main blockchain. In an illustrative example, the reference to the preceding data block may include a cryptographic hash of the previous block, as described in more detail herein above.

At block 690, the computing device may broadcast the current data block of the main blockchain to a plurality of blockchain nodes.

At block 695, the computing device may utilize the digital representation of the dental anatomy to generate instructions to manage a treatment plan using the first digital representation of dental anatomy.

Figure 7:
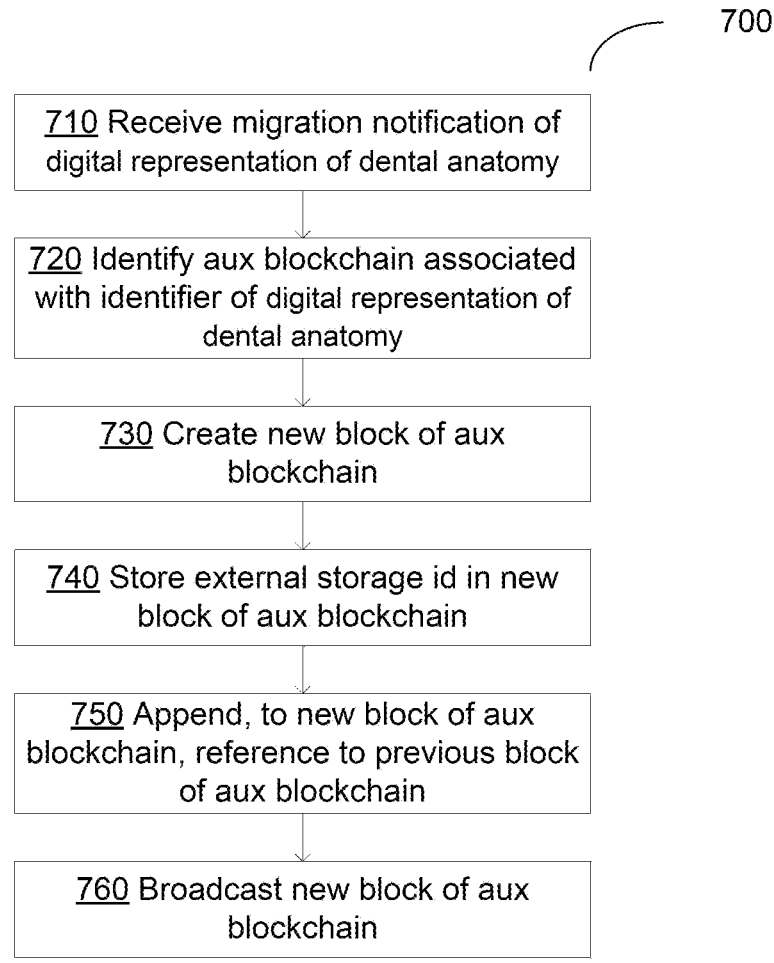
FIG. 7 depicts a flow diagram of one illustrative example of a method of updating the two-dimensional blockchain structure to reflect migration of digital representations of dental anatomy to a new external storage location, in accordance with one or more aspects of the present disclosure.

FIG. 7 depicts a flow diagram of one illustrative example of a method of updating the two-dimensional blockchain structure to reflect migration of digital representations of dental anatomy to a new external storage location, in accordance with one or more aspects of the present disclosure. Method 700 and/or each of its individual functions, routines, subroutines, or operations may be performed by one or more processors of the computer system (e.g., example computing device 900 of FIG. 9) executing the method. In some implementations, method 700 may be performed by a single processing thread. Alternatively, method 700 may be performed by two or more processing threads, each thread executing one or more individual functions, routines, subroutines, or operations of the method. In an illustrative example, the processing threads implementing method 700 may be synchronized (e.g., using semaphores, critical sections, and/or other thread synchronization mechanisms). Alternatively, the processing threads implementing method 700 may be executed asynchronously with respect to each other. Therefore, while FIG. 7 and the associated description lists the operations of method 700 in certain order, various implementations of the method may perform at least some of the described operations in parallel and/or in arbitrary selected orders.

At block 710, a computing device implementing the method may receive a notification that a previously stored digital representation of dental anatomy has been migrated to a new external storage location. The notification may include the patient identifier and the image identifier (e.g., the date of acquiring the image), as described in more detail herein above. In various illustrative examples, the notification may be received via a communication socket, via an application programming interface (API) call, or via another suitable inter-process communication mechanism.

At block 720, the computing device may identify (e.g., using the patient identifier and the image identifier) the auxiliary blockchain which is utilized for storing the external storage locations of the digital representations of dental anatomy.

At block 730, the computing device may create a new data block of the auxiliary blockchain.

At block 740, the computing device may store, in the newly created data block, an identifier of the external storage location (e.g., in the form of a URI) in which the digital representation of dental anatomy is stored after migration.

At block 750, the computing device may append, to the newly created data block of the auxiliary blockchain, a reference to the previous data block of the auxiliary blockchain. In an illustrative example, the reference to the previous data block may include a cryptographic hash of the previous block, as described in more detail herein above.

At block 760, the computing device may broadcast the second data block of the auxiliary blockchain to the plurality of blockchain nodes, and the method may terminate.

Figure 8:
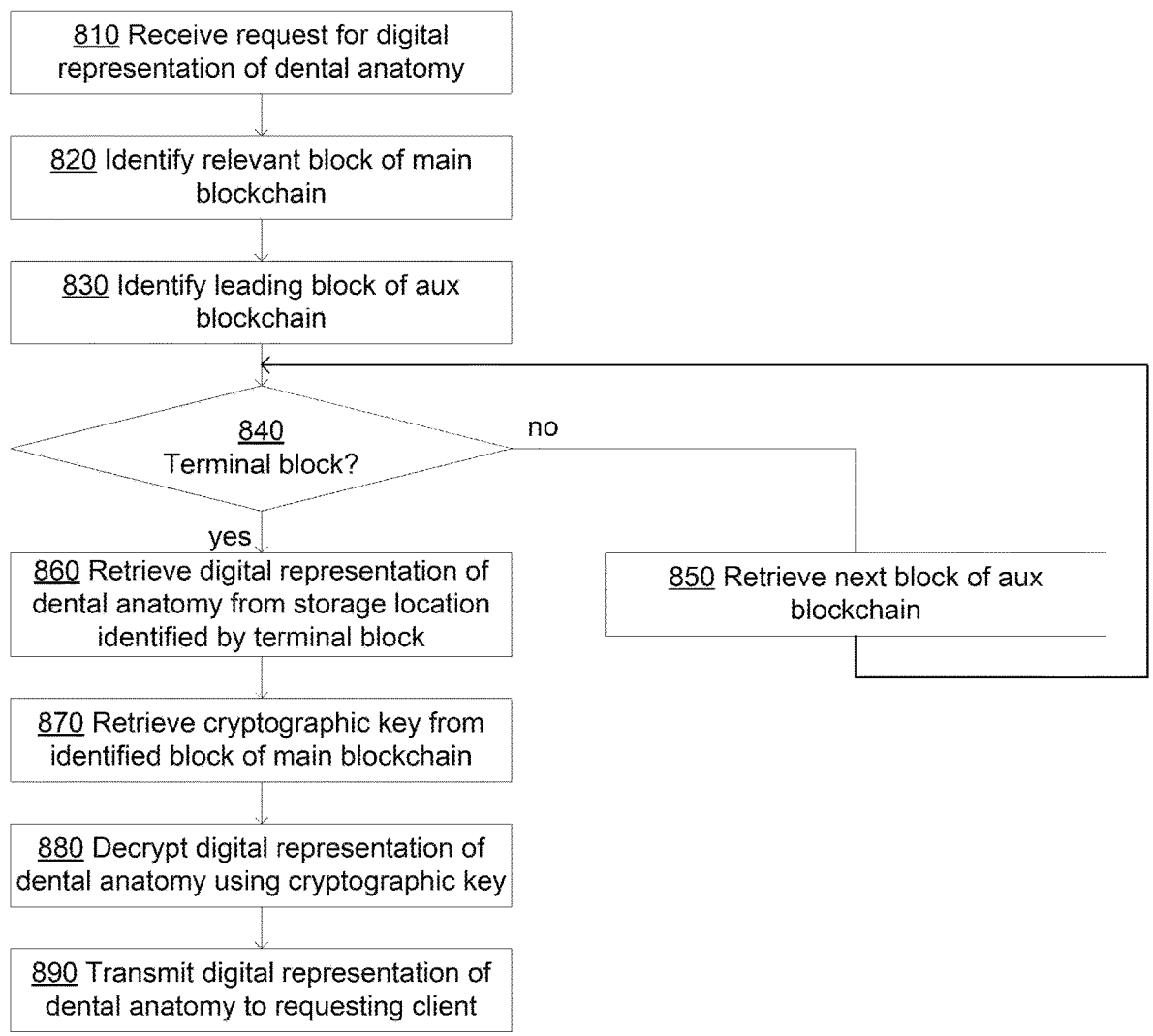
FIG. 8 depicts a flow diagram of one illustrative example of a method 800 of servicing digital representation of dental anatomy requests, in accordance with one or more aspects of the present disclosure, in accordance with one or more aspects of the present disclosure.

FIG. 8 depicts a flow diagram of one illustrative example of a method 800 of servicing digital representation of dental anatomy requests, in accordance with one or more aspects of the present disclosure. Method 800 and/or each of its individual functions, routines, subroutines, or operations may be performed by one or more processors of the computer system (e.g., example computing device 900 of FIG. 9) executing the method. In some implementations, method 800 may be performed by a single processing thread. Alternatively, method 800 may be performed by two or more processing threads, each thread executing one or more individual functions, routines, subroutines, or operations of the method. In an illustrative example, the processing threads implementing method 800 may be synchronized (e.g., using semaphores, critical sections, and/or other thread synchronization mechanisms). Alternatively, the processing threads implementing method 800 may be executed asynchronously with respect to each other. Therefore, while FIG. 8 and the associated description lists the operations of method 800 in certain order, various implementations of the method may perform at least some of the described operations in parallel and/or in arbitrary selected orders.

At block 810, a computing device implementing the method may receive a digital representation of dental anatomy request specifying a digital representation of dental anatomy identifier (e.g., a patient identifier and a date of a medical event, such as a patient visit, a diagnostic procedure and/or treatment performed, an intraoral scan acquired, etc.). In various illustrative examples, the digital representation of dental anatomy request may be received via a communication socket, via an application programming interface (API) call, or via another suitable inter-process communication mechanism. The digital representation of dental anatomy request may be initiated by a digital representation of dental anatomy management client device, as described in more detail herein above.

At block 820, the computing device may identify, among a plurality of data blocks of the main blockchain, the data block which stores the digital representation of dental anatomy data item identified by the digital representation of dental anatomy identifier, as described in more detail herein above.

At block 830, the computing device may identify the leading data block of the auxiliary blockchain, such that the leading data block of the auxiliary blockchain is referenced by the previously identified data block of the main blockchain, as described in more detail herein above.

Responsive to determining, at block 840, that the current data block of the auxiliary blockchain is the terminal block of the auxiliary blockchain, the computing device may, at block 850, retrieving the digital representation of dental anatomy from the external storage location referenced by the terminal data block of the auxiliary blockchain; otherwise, at block 860, the computing device may retrieve the next data block of the auxiliary blockchain.

At block 870, the computing device may retrieve, from the previously identified block of the main blockchain, the cryptographic key utilized for encrypting/decrypting the digital representation of dental anatomy associated with the digital representation of dental anatomy, as described in more detail herein above.

At block 880, the computing device may decrypt the retrieved digital representation of dental anatomy using the cryptographic key, as described in more detail herein above.

At block 890, the computing device may transmit the digital representation of dental anatomy and one or more associated medical record data items to the digital representation of dental anatomy management client device, and the method may terminate.

As noted herein above, while specific examples described herein are related to orthodontic treatments, the systems and methods of the present disclosure may similarly be employed by in dentistry (including prosthodontic (restorative and cosmetic) and orthodontic procedures), oral surgery, and/or various other medical areas in which two-dimensional images, three-dimensional images and/or other multimedia content of medical records may be utilized.

Figure 9:
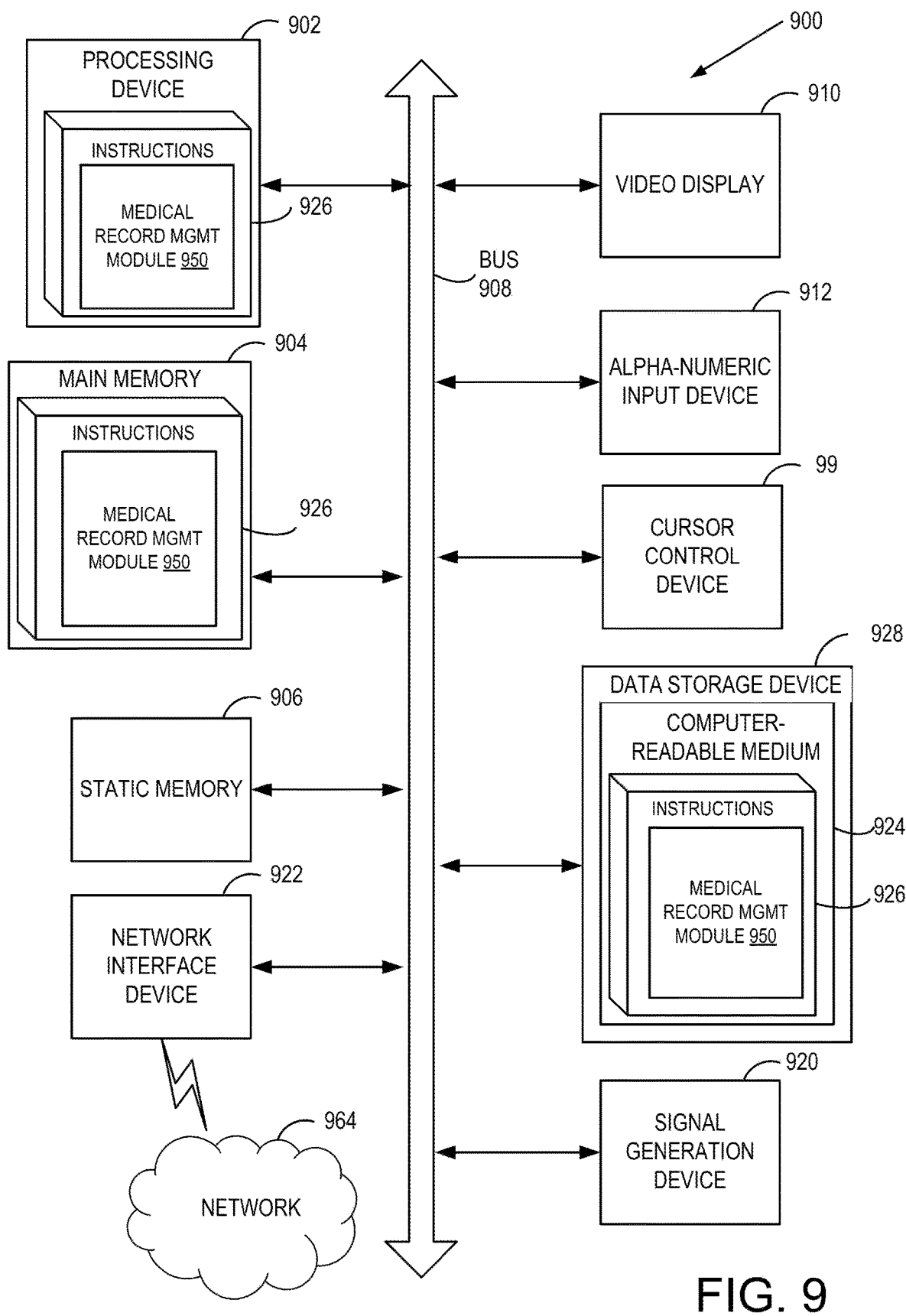
FIG. 9 illustrates a diagrammatic representation of a machine in the example form of a computing device within which a set of instructions, for causing the machine to perform the methods described herein.

FIG. 9 illustrates a diagrammatic representation of a machine in the example form of a computing device 900 within which a set of instructions, for causing the machine to perform any one or more of the methodologies discussed herein (e.g., the methods of FIGS. 6-8). In some embodiments, the machine may be part of a design station or communicatively coupled to the design station. In alternative embodiments, the machine may be connected (e.g., networked) to other machines in a Local Area Network (LAN), an intranet, an extranet, or the Internet. For example, the machine may be networked to the design station and/or a rapid prototyping apparatus such as a 3D printer or SLA apparatus. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computing device 900 includes a processing device 902, a main memory 904 (e.g., read-only memory (ROM), flash memory, dynamic random access memory (DRAM) such as synchronous DRAM (SDRAM), etc.), a static memory 906 (e.g., flash memory, static random access memory (SRAM), etc.), and a secondary memory (e.g., a data storage device 928), which communicate with each other via a bus 908.

Processing device 902 represents one or more general-purpose processors such as a microprocessor, central processing unit, or the like. More particularly, the processing device 902 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 902 may also be one or more special-purpose processing devices such as an application specific integrated circuit (ASIC), a field programmable gate array (FPGA), a digital signal processor (DSP), network processor, or the like. Processing device 902 is configured to execute the processing logic (instructions 926) for performing operations and steps discussed herein.

The computing device 900 may further include a network interface device 922 for communicating with a network 964. The computing device 900 also may include a video display unit 910 (e.g., a liquid crystal display (LCD) or a cathode ray tube (CRT)), an alphanumeric input device 912 (e.g., a keyboard), a cursor control device 99 (e.g., a mouse), and a signal generation device 920 (e.g., a speaker).

The data storage device 928 may include a machine-readable storage medium (or more specifically a non-transitory computer-readable storage medium) 924 on which is stored one or more sets of instructions 926 embodying any one or more of the methodologies or functions described herein. A non-transitory storage medium refers to a storage medium other than a carrier wave. The instructions 926 may also reside, completely or at least partially, within the main memory 904 and/or within the processing device 902 during execution thereof by the computer device 900, the main memory 904 and the processing device 902 also constituting computer-readable storage media.

The computer-readable storage medium 924 may also be used to store one or more digital models of aligners and/or dental arches (also referred to as electronic models), medical data such as 2D and/or 3D images of teeth, dental arches, smiles, etc. and/or an medical record management module 950, which may perform one or more of the operations of the methods described herein. The computer readable storage medium 924 may also store a software library containing methods that call the digital representation of dental anatomy management 950. While the computer-readable storage medium 924 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing or encoding a set of instructions for execution by the machine and that cause the machine to perform any one or more of the methodologies of the present disclosure. The term "computer-readable storage medium" shall accordingly be taken to include, but not be limited to, solid-state memories, and optical and magnetic media.

FIG. 10 illustrates an exemplary tooth repositioning appliance or aligner 1000 that can be worn by a patient in order to achieve an incremental repositioning of individual teeth 1002 in the jaw. The appliance can include a shell (e.g., a continuous polymeric shell or a segmented shell) having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. A "polymeric material," as used herein, may include any material formed from a polymer.

The aligner 1000 can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, some, most, or even all of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements 1004 on teeth 1002 with corresponding receptacles or apertures 1006 in the appliance 1000 so that the appliance can apply a selected force on the tooth.

Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309,210 and 6,830,450.

FIG. 11 illustrates a tooth repositioning system 1111 including a plurality of appliances 1112, 1114, 1116. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 1111 can include a first appliance 1112 corresponding to an initial tooth arrangement, one or more intermediate appliances 1114 corresponding to one or more intermediate arrangements, and a final appliance 1116 corresponding to a target arrangement. A target tooth arrangement can be a planned final tooth arrangement selected for the patient's teeth at the end of all planned dental (e.g., orthodontic) treatment. Alternatively, a target arrangement can be one of some intermediate arrangements for the patient's teeth during the course of the treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

In some embodiments, the appliances 1112, 1114, 1116 (or portions thereof) can be produced using indirect fabrication techniques, such as by thermoforming over a positive or negative mold. Indirect fabrication of an orthodontic appliance can involve producing a positive or negative mold of the patient's dentition in a target arrangement (e.g., by rapid prototyping, milling, etc.) and thermoforming one or more sheets of material over the mold in order to generate an appliance shell.

In an example of indirect fabrication, a mold of a patient's dental arch may be fabricated from a digital model of the dental arch, and a shell may be formed over the mold (e.g., by thermoforming a polymeric sheet over the mold of the dental arch and then trimming the thermoformed polymeric sheet). The fabrication of the mold may be performed by a rapid prototyping machine (e.g., a stereolithography (SLA) 3D printer). The rapid prototyping machine may receive digital models of molds of dental arches and/or digital models of the appliances 1112, 1114, 1116 after the digital models of the appliances 1112, 1114, 1116 have been processed by processing logic of a computing device, such as the computing device in FIG. 9. The processing logic may include hardware (e.g., circuitry, dedicated logic, programmable logic, microcode, etc.), software (e.g., instructions executed by a processing device), firmware, or a combination thereof. For example, one or more operations may be performed by a processing device executing an appliance design analysis program or module 1450.

To manufacture the molds, a shape of a dental arch for a patient at a treatment stage is determined based on a treatment plan. In the example of orthodontics, the treatment plan may be generated based on an intraoral scan of a dental arch to be modeled. The intraoral scan of the patient's dental arch may be performed to generate a three dimensional (3D) virtual model of the patient's dental arch (mold). For example, a full scan of the mandibular and/or maxillary arches of a patient may be performed to generate 3D virtual models thereof. The intraoral scan may be performed by creating multiple overlapping intraoral images from different scanning stations and then stitching together the intraoral images to provide a composite 3D virtual model. In other applications, virtual 3D models may also be generated based on scans of an object to be modeled or based on use of computer aided drafting techniques (e.g., to design the virtual 3D mold). Alternatively, an initial negative mold may be generated from an actual object to be modeled (e.g., a dental impression or the like). The negative mold may then be scanned to determine a shape of a positive mold that will be produced. An intraoral scan of a patient may be medical data that can be stored in a medical record using a blockchain as described herein above. Additionally, or alternatively, one or more virtual 3D models may be medical data that can be stored in a medical record using a blockchain as described herein above.

Once the virtual 3D model of the patient's dental arch is generated, a dental practitioner may determine a desired treatment outcome, which includes final positions and orientations for the patient's teeth. Processing logic may then determine a number of treatment stages to cause the teeth to progress from starting positions and orientations to the target final positions and orientations. The shape of the final virtual 3D model and each intermediate virtual 3D model may be determined by computing the progression of tooth movement throughout dental (e.g., orthodontic) treatment from initial tooth placement and orientation to final corrected tooth placement and orientation. For each treatment stage, a separate virtual 3D model of the patient's dental arch at that treatment stage may be generated. The shape of each virtual 3D model will be different. The original virtual 3D model, the final virtual 3D model and each intermediate virtual 3D model is unique and customized to the patient.

Accordingly, multiple different virtual 3D models (digital designs) of a dental arch may be generated for a single patient. A first virtual 3D model may be a unique model of a patient's dental arch and/or teeth as they presently exist, and a final virtual 3D model may be a model of the patient's dental arch and/or teeth after correction of one or more teeth and/or a jaw. Multiple intermediate virtual 3D models may be modeled, each of which may be incrementally different from previous virtual 3D models. Medical data that is stored in a medical record may include one or more of the virtual 3D models.

Each virtual 3D model of a patient's dental arch may be used to generate a unique customized physical mold of the dental arch at a particular stage of treatment. The shape of the mold may be at least in part based on the shape of the virtual 3D model for that treatment stage. The virtual 3D model may be represented in a file such as a computer aided drafting (CAD) file or a 3D printable file such as a stereolithography (STL) file. The virtual 3D model for the mold may be sent to a third party (e.g., clinician office, laboratory, manufacturing facility or other entity). The virtual 3D model may include instructions that will control a fabrication system or device in order to produce the mold with specified geometries.

A clinician office, laboratory, manufacturing facility or other entity may receive the virtual 3D model of the mold, the digital model having been created as set forth above. The entity may input the digital model into a rapid prototyping machine. The rapid prototyping machine then manufactures the mold using the digital model. One example of a rapid prototyping manufacturing machine is a 3D printer. 3D printing includes any layer-based additive manufacturing processes. 3D printing may be achieved using an additive process, where successive layers of material are formed in proscribed shapes. 3D printing may be performed using extrusion deposition, granular materials binding, lamination, photopolymerization, continuous liquid interface production (CLIP), or other techniques. 3D printing may also be achieved using a subtractive process, such as milling.

In some instances, stereolithography (SLA), also known as optical fabrication solid imaging, is used to fabricate an SLA mold. In SLA, the mold is fabricated by successively printing thin layers of a photo-curable material (e.g., a polymeric resin) on top of one another. A platform rests in a bath of a liquid photopolymer or resin just below a surface of the bath. A light source (e.g., an ultraviolet laser) traces a pattern over the platform, curing the photopolymer where the light source is directed, to form a first layer of the mold. The platform is lowered incrementally, and the light source traces a new pattern over the platform to form another layer of the mold at each increment. This process repeats until the mold is completely fabricated. Once all of the layers of the mold are formed, the mold may be cleaned and cured.

Materials such as a polyester, a co-polyester, a polycarbonate, a polycarbonate, a thermopolymeric polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, a styrenic block copolymer (SBC), a silicone rubber, an elastomeric alloy, a thermopolymeric elastomer (TPE), a thermopolymeric vulcanizate (TPV) elastomer, a polyurethane elastomer, a block copolymer elastomer, a polyolefin blend elastomer, a thermopolymeric co-polyester elastomer, a thermopolymeric polyamide elastomer, or combinations thereof, may be used to directly form the mold. The materials used for fabrication of the mold can be provided in an uncured form (e.g., as a liquid, resin, powder, etc.) and can be cured (e.g., by photopolymerization, light curing, gas curing, laser curing, crosslinking, etc.). The properties of the material before curing may differ from the properties of the material after curing.

Appliances may be formed from each mold and when applied to the teeth of the patient, may provide forces to move the patient's teeth as dictated by the treatment plan. The shape of each appliance is unique and customized to a particular patient and a particular treatment stage. In an example, the appliances 1112, 1114, 1116 can be pressure formed or thermoformed over the molds. Each mold may be used to fabricate an appliance that will apply forces to the patient's teeth at a particular stage of the treatment. The appliances 1112, 1114, 1116 each have teeth-receiving cavities that receive and resiliently reposition the teeth in accordance with a particular treatment stage.

In one embodiment, a sheet of material is pressure formed or thermoformed over the mold. The sheet may be, for example, a sheet of polymeric (e.g., an elastic thermopolymeric, a sheet of polymeric material, etc.). To thermoform the shell over the mold, the sheet of material may be heated to a temperature at which the sheet becomes pliable. Pressure may concurrently be applied to the sheet to form the now pliable sheet around the mold. Once the sheet cools, it will have a shape that conforms to the mold. In one embodiment, a release agent (e.g., a non-stick material) is applied to the mold before forming the shell. This may facilitate later removal of the mold from the shell. Forces may be applied to lift the appliance from the mold. In some instances, a breakage, warpage, or deformation may result from the removal forces. Accordingly, embodiments disclosed herein may determine where the probable point or points of damage may occur in a digital design of the appliance prior to manufacturing and may perform a corrective action.

Additional information may be added to the appliance. The additional information may be any information that pertains to the appliance. Examples of such additional information includes a part number identifier, patient name, a patient identifier, a case number, a sequence identifier (e.g., indicating which appliance a particular liner is in a treatment sequence), a date of manufacture, a clinician name, a logo and so forth. For example, after determining there is a probable point of damage in a digital design of an appliance, an indicator may be inserted into the digital design of the appliance. The indicator may represent a recommended place to begin removing the polymeric appliance to prevent the point of damage from manifesting during removal in some embodiments. Such additional information may be included in a medical record, which may be stored using blockchain techniques described herein.

After an appliance is formed over a mold for a treatment stage, that appliance is subsequently trimmed along a cutline (also referred to as a trim line) and the appliance may be removed from the mold. The processing logic may determine a cutline for the appliance. The determination of the cutline(s) may be made based on the virtual 3D model of the dental arch at a particular treatment stage, based on a virtual 3D model of the appliance to be formed over the dental arch, or a combination of a virtual 3D model of the dental arch and a virtual 3D model of the appliance. The location and shape of the cutline can be important to the functionality of the appliance (e.g., an ability of the appliance to apply desired forces to a patient's teeth) as well as the fit and comfort of the appliance. For shells such as orthodontic appliances, orthodontic retainers and orthodontic splints, the trimming of the shell may play a role in the efficacy of the shell for its intended purpose (e.g., aligning, retaining or positioning one or more teeth of a patient) as well as the fit of the shell on a patient's dental arch. For example, if too much of the shell is trimmed, then the shell may lose rigidity and an ability of the shell to exert force on a patient's teeth may be compromised. When too much of the shell is trimmed, the shell may become weaker at that location and may be a point of damage when a patient removes the shell from their teeth or when the shell is removed from the mold. In some embodiments, the cut line may be modified in the digital design of the appliance as one of the corrective actions taken when a probable point of damage is determined to exist in the digital design of the appliance.

On the other hand, if too little of the shell is trimmed, then portions of the shell may impinge on a patient's gums and cause discomfort, swelling, and/or other dental issues. Additionally, if too little of the shell is trimmed at a location, then the shell may be too rigid at that location. In some embodiments, the cutline may be a straight line across the appliance at the gingival line, below the gingival line, or above the gingival line. In some embodiments, the cutline may be a gingival cutline that represents an interface between an appliance and a patient's gingiva. In such embodiments, the cutline controls a distance between an edge of the appliance and a gum line or gingival surface of a patient.

Each patient has a unique dental arch with unique gingiva. Accordingly, the shape and position of the cutline may be unique and customized for each patient and for each stage of treatment. For instance, the cutline is customized to follow along the gum line (also referred to as the gingival line). In some embodiments, the cutline may be away from the gum line in some regions and on the gum line in other regions. For example, it may be desirable in some instances for the cutline to be away from the gum line (e.g., not touching the gum) where the shell will touch a tooth and on the gum line (e.g., touching the gum) in the interproximal regions between teeth. Accordingly, it is important that the shell be trimmed along a predetermined cutline.

In some embodiments, the orthodontic appliances herein (or portions thereof) can be produced using direct fabrication, such as additive manufacturing techniques (also referred to herein as "3D printing) or subtractive manufacturing techniques (e.g., milling). In some embodiments, direct fabrication involves forming an object (e.g., an orthodontic appliance or a portion thereof) without using a physical template (e.g., mold, mask etc.) to define the object geometry. Additive manufacturing techniques can be categorized as follows: (1) vat photopolymerization (e.g., stereolithography), in which an object is constructed layer by layer from a vat of liquid photopolymer resin; (2) material jetting, in which material is jetted onto a build platform using either a continuous or drop on demand (DOD) approach; (3) binder jetting, in which alternating layers of a build material (e.g., a powder-based material) and a binding material (e.g., a liquid binder) are deposited by a print head; (4) fused deposition modeling (FDM), in which material is drawn though a nozzle, heated, and deposited layer by layer; (5) powder bed fusion, including but not limited to direct metal laser sintering (DMLS), electron beam melting (EBM), selective heat sintering (SHS), selective laser melting (SLM), and selective laser sintering (SLS); (6) sheet lamination, including but not limited to laminated object manufacturing (LOM) and ultrasonic additive manufacturing (UAM); and (7) directed energy deposition, including but not limited to laser engineering net shaping, directed light fabrication, direct metal deposition, and 3D laser cladding. For example, stereolithography can be used to directly fabricate one or more of the appliances 1112, 1114, 1116. In some embodiments, stereolithography involves selective polymerization of a photosensitive resin (e.g., a photopolymer) according to a desired cross-sectional shape using light (e.g., ultraviolet light). The object geometry can be built up in a layer-by-layer fashion by sequentially polymerizing a plurality of object cross-sections. As another example, the appliances 1112, 1114, 1116 can be directly fabricated using selective laser sintering. In some embodiments, selective laser sintering involves using a laser beam to selectively melt and fuse a layer of powdered material according to a desired cross-sectional shape in order to build up the object geometry. As yet another example, the appliances 1112, 1114, 1116 can be directly fabricated by fused deposition modeling. In some embodiments, fused deposition modeling involves melting and selectively depositing a thin filament of thermoplastic polymer in a layer-by-layer manner in order to form an object. In yet another example, material jetting can be used to directly fabricate the appliances 1112, 1114, 1116. In some embodiments, material jetting involves jetting or extruding one or more materials onto a build surface in order to form successive layers of the object geometry.

In some embodiments, the direct fabrication methods provided herein build up the object geometry in a layer-by-layer fashion, with successive layers being formed in discrete build steps. Alternatively or in combination, direct fabrication methods that allow for continuous build-up of an object geometry can be used, referred to herein as "continuous direct fabrication." Various types of continuous direct fabrication methods can be used. As an example, in some embodiments, the appliances 1112, 1114, 1116 are fabricated using "continuous liquid interphase printing," in which an object is continuously built up from a reservoir of photopolymerizable resin by forming a gradient of partially cured resin between the building surface of the object and a polymerization-inhibited "dead zone." In some embodiments, a semi-permeable membrane is used to control transport of a photopolymerization inhibitor (e.g., oxygen) into the dead zone in order to form the polymerization gradient. Continuous liquid interphase printing can achieve fabrication speeds about 25 times to about 110 times faster than other direct fabrication methods, and speeds about 1100 times faster can be achieved with the incorporation of cooling systems. Continuous liquid interphase printing is described in U.S. Patent Publication Nos. 2011/0097311, 2011/0097316, and 2011/0112532, the disclosures of each of which are incorporated herein by reference in their entirety.

As another example, a continuous direct fabrication method can achieve continuous build-up of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved. Such methods are described in U.S. Pat. No. 7,892,474, the disclosure of which is incorporated herein by reference in its entirety.

In another example, a continuous direct fabrication method can involve extruding a composite material composed of a curable liquid material surrounding a solid strand. The composite material can be extruded along a continuous three-dimensional path in order to form the object. Such methods are described in U.S. Patent Publication No. 2014/0061974, the disclosure of which is incorporated herein by reference in its entirety.

In yet another example, a continuous direct fabrication method utilizes a "heliolithography" approach in which the liquid photopolymer is cured with focused radiation while the build platform is continuously rotated and raised. Accordingly, the object geometry can be continuously built up along a spiral build path. Such methods are described in U.S. Patent Publication No. 2014/0265034, the disclosure of which is incorporated herein by reference in its entirety.

The direct fabrication approaches provided herein are compatible with a wide variety of materials, including but not limited to one or more of the following: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyamide elastomer, a thermoset material, or combinations thereof. The materials used for direct fabrication can be provided in an uncured form (e.g., as a liquid, resin, powder, etc.) and can be cured (e.g., by photopolymerization, light curing, gas curing, laser curing, crosslinking, etc.) in order to form an orthodontic appliance or a portion thereof. The properties of the material before curing may differ from the properties of the material after curing. Once cured, the materials herein can exhibit sufficient strength, stiffness, durability, biocompatibility, etc. for use in an orthodontic appliance. The post-curing properties of the materials used can be selected according to the desired properties for the corresponding portions of the appliance.

In some embodiments, relatively rigid portions of the orthodontic appliance can be formed via direct fabrication using one or more of the following materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, and/or a polytrimethylene terephthalate.

In some embodiments, relatively elastic portions of the orthodontic appliance can be formed via direct fabrication using one or more of the following materials: a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, and/or a thermoplastic polyamide elastomer.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated before, during, and/or at the end of each build, and/or at predetermined time intervals (e.g., every $n^{th}$ build, once per hour, once per day, once per week, etc.), depending on the stability of the system. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

Optionally, the direct fabrication methods described herein allow for fabrication of an appliance including multiple materials, referred to herein as "multi-material direct fabrication." In some embodiments, a multi-material direct fabrication method involves concurrently forming an object from multiple materials in a single manufacturing step. For instance, a multi-tip extrusion apparatus can be used to selectively dispense multiple types of materials from distinct material supply sources in order to fabricate an object from a plurality of different materials. Such methods are described in U.S. Pat. No. 6,749,414, the disclosure of which is incorporated herein by reference in its entirety. Alternatively or in combination, a multi-material direct fabrication method can involve forming an object from multiple materials in a plurality of sequential manufacturing steps. For instance, a first portion of the object can be formed from a first material in accordance with any of the direct fabrication methods herein, then a second portion of the object can be formed from a second material in accordance with methods herein, and so on, until the entirety of the object has been formed.

Direct fabrication can provide various advantages compared to other manufacturing approaches. For instance, in contrast to indirect fabrication, direct fabrication permits production of an orthodontic appliance without utilizing any molds or templates for shaping the appliance, thus reducing the number of manufacturing steps involved and improving the resolution and accuracy of the final appliance geometry. Additionally, direct fabrication permits precise control over the three-dimensional geometry of the appliance, such as the appliance thickness. Complex structures and/or auxiliary components can be formed integrally as a single piece with the appliance shell in a single manufacturing step, rather than being added to the shell in a separate manufacturing step. In some embodiments, direct fabrication is used to produce appliance geometries that would be difficult to create using alternative manufacturing techniques, such as appliances with very small or fine features, complex geometric shapes, undercuts, interproximal structures, shells with variable thicknesses, and/or internal structures (e.g., for improving strength with reduced weight and material usage). For example, in some embodiments, the direct fabrication approaches herein permit fabrication of an orthodontic appliance with feature sizes of less than or equal to about 5 µm, or within a range from about 5 µm to about 50 µm, or within a range from about 20 µm to about 50 µm.

The direct fabrication techniques described herein can be used to produce appliances with substantially isotropic material properties, e.g., substantially the same or similar strengths along all directions. In some embodiments, the direct fabrication approaches herein permit production of an orthodontic appliance with a strength that varies by no more than about 25%, about 20%, about 11%, about 11%, about 5%, about 1%, or about 0.5% along all directions. Additionally, the direct fabrication approaches herein can be used to produce orthodontic appliances at a faster speed compared to other manufacturing techniques. In some embodiments, the direct fabrication approaches herein allow for production of an orthodontic appliance in a time interval less than or equal to about 1 hour, about 30 minutes, about 25 minutes, about 20 minutes, about 11 minutes, about 11 minutes, about 5 minutes, about 4 minutes, about 3 minutes, about 2 minutes, about 1 minutes, or about 30 seconds. Such manufacturing speeds allow for rapid "chair-side" production of customized appliances, e.g., during a routine appointment or checkup.

In some embodiments, the direct fabrication methods described herein implement process controls for various machine parameters of a direct fabrication system or device in order to ensure that the resultant appliances are fabricated with a high degree of precision. Such precision can be beneficial for ensuring accurate delivery of a desired force system to the teeth in order to effectively elicit tooth movements. Process controls can be implemented to account for process variability arising from multiple sources, such as the material properties, machine parameters, environmental variables, and/or post-processing parameters.

Material properties may vary depending on the properties of raw materials, purity of raw materials, and/or process variables during mixing of the raw materials. In many embodiments, resins or other materials for direct fabrication should be manufactured with tight process control to ensure little variability in photo-characteristics, material properties (e.g., viscosity, surface tension), physical properties (e.g., modulus, strength, elongation) and/or thermal properties (e.g., glass transition temperature, heat deflection temperature). Process control for a material manufacturing process can be achieved with screening of raw materials for physical properties and/or control of temperature, humidity, and/or other process parameters during the mixing process. By implementing process controls for the material manufacturing procedure, reduced variability of process parameters and more uniform material properties for each batch of material can be achieved. Residual variability in material properties can be compensated with process control on the machine, as discussed further herein.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated at the end of each build. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

In many embodiments, environmental variables (e.g., temperature, humidity, Sunlight or exposure to other energy/curing source) are maintained in a tight range to reduce variable in appliance thickness and/or other properties. Optionally, machine parameters can be adjusted to compensate for environmental variables.

In many embodiments, post-processing of appliances includes cleaning, post-curing, and/or support removal processes. Relevant post-processing parameters can include purity of cleaning agent, cleaning pressure and/or temperature, cleaning time, post-curing energy and/or time, and/or consistency of support removal process. These parameters can be measured and adjusted as part of a process control scheme. In addition, appliance physical properties can be varied by modifying the post-processing parameters. Adjusting post-processing machine parameters can provide another way to compensate for variability in material properties and/or machine properties.

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled rapid prototyping such as 3D printing, etc.). The computer-based methods presented herein can improve the accuracy, flexibility, and convenience of appliance fabrication.

FIG. 12 illustrates a method 1250 of orthodontic treatment using a plurality of appliances, in accordance with embodiments. The method 1250 can be practiced using any of the appliances or appliance sets described herein. In block 1260, a first orthodontic appliance is applied to a patient's teeth in order to reposition the teeth from a first tooth arrangement to a second tooth arrangement. In block 1270, a second orthodontic appliance is applied to the patient's teeth in order to reposition the teeth from the second tooth arrangement to a third tooth arrangement. The method 1250 can be repeated as necessary using any suitable number and combination of sequential appliances in order to incrementally reposition the patient's teeth from an initial arrangement to a target arrangement. The appliances can be generated all at the same stage or in sets or batches (e.g., at the beginning of a stage of the treatment), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance. Images may be taken of a patient's smile during different stages of orthodontic treatment (e.g., after one or more appliances have been worn). Such images may be stored in a patient medical record using the blockchain techniques described herein above.

Figure 13:
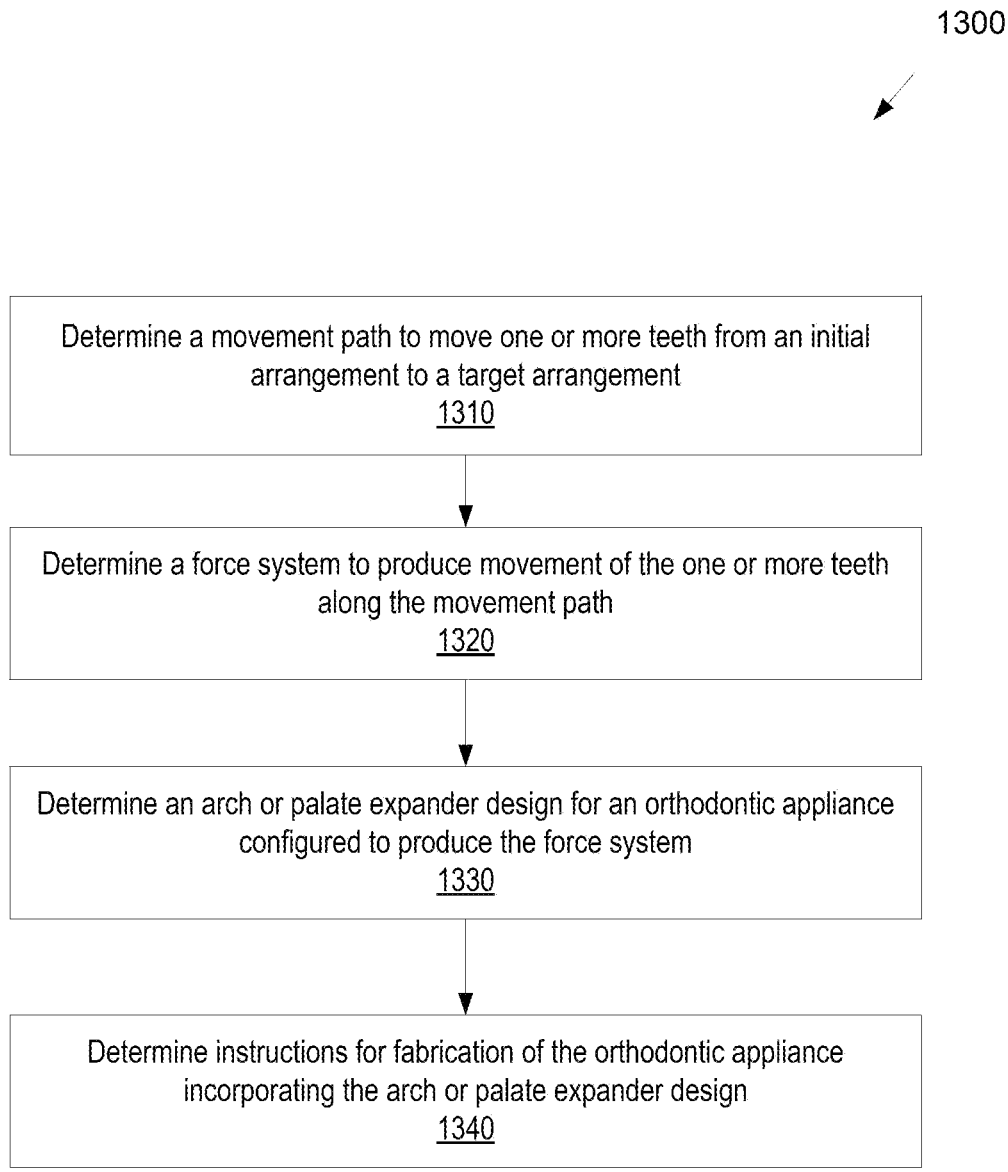
FIG. 13 illustrates a method for designing an orthodontic appliance, in accordance with embodiments.

FIG. 13 illustrates a method 1300 for designing an orthodontic appliance to be produced by direct fabrication, in accordance with embodiments. The method 1300 can be applied to any embodiment of the orthodontic appliances described herein. Some or all of the blocks of the method 1300 can be performed by any suitable data processing system or device, e.g., one or more processors configured with suitable instructions.

In block 1310, a movement path to move one or more teeth from an initial arrangement to a target arrangement is determined. The initial arrangement can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. From the obtained data, a digital data set can be derived that represents the initial (e.g., pretreatment) arrangement of the patient's teeth and other tissues. Optionally, the initial digital data set is processed to segment the tissue constituents from each other. For example, data structures that digitally represent individual tooth crowns can be produced. Advantageously, digital models of entire teeth can be produced, including measured or extrapolated hidden surfaces and root structures, as well as surrounding bone and soft tissue.

The target arrangement of the teeth (e.g., a desired and intended end result of orthodontic treatment) can be received from a clinician in the form of a prescription, can be calculated from basic orthodontic principles, and/or can be extrapolated computationally from a clinical prescription. With a specification of the desired final positions of the teeth and a digital representation of the teeth themselves, the final position and surface geometry of each tooth can be specified to form a complete model of the tooth arrangement at the desired end of treatment.

Having both an initial position and a target position for each tooth, a movement path can be defined for the motion of each tooth. In some embodiments, the movement paths are configured to move the teeth in the quickest fashion with the least amount of round-tripping to bring the teeth from their initial positions to their desired target positions. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions, so that moving from one point to the next in the sequence does not result in a collision of teeth.

In block 1320, a force system to produce movement of the one or more teeth along the movement path is determined. A force system can include one or more forces and/or one or more torques. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

The determination of the force system can include constraints on the allowable forces, such as allowable directions and magnitudes, as well as desired motions to be brought about by the applied forces. For example, in fabricating palatal expanders, different movement strategies may be desired for different patients. For example, the amount of force needed to separate the palate can depend on the age of the patient, as very young patients may not have a fully-formed suture. Thus, in juvenile patients and others without fully-closed palatal sutures, palatal expansion can be accomplished with lower force magnitudes. Slower palatal movement can also aid in growing bone to fill the expanding suture. For other patients, a more rapid expansion may be desired, which can be achieved by applying larger forces.

These requirements can be incorporated as needed to choose the structure and materials of appliances; for example, by choosing palatal expanders capable of applying large forces for rupturing the palatal suture and/or causing rapid expansion of the palate. Subsequent appliance stages can be designed to apply different amounts of force, such as first applying a large force to break the suture, and then applying smaller forces to keep the suture separated or gradually expand the palate and/or arch.

The determination of the force system can also include modeling of the facial structure of the patient, such as the skeletal structure of the jaw and palate. Scan data of the palate and arch, such as X-ray data or 3D optical scanning data, for example, can be used to determine parameters of the skeletal and muscular system of the patient's mouth, so as to determine forces sufficient to provide a desired expansion of the palate and/or arch. Such data may be included in a digital representation of dental anatomy of a patient, which may be stored in accordance with embodiments discussed herein. In some embodiments, the thickness and/or density of the mid-palatal suture may be measured, or input by a treating professional. In other embodiments, the treating professional can select an appropriate treatment based on physiological characteristics of the patient. For example, the properties of the palate may also be estimated based on factors such as the patient's age—for example, young juvenile patients will typically require lower forces to expand the suture than older patients, as the suture has not yet fully formed.

In block 1330, an arch or palate expander design for an orthodontic appliance configured to produce the force system is determined. Determination of the arch or palate expander design, appliance geometry, material composition, and/or properties can be performed using a treatment or force application simulation environment. A simulation environment can include, e.g., computer modeling systems, biomechanical systems or apparatus, and the like. Optionally, digital models of the appliance and/or teeth can be produced, such as finite element models. The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, CA. For creating finite element models and analyzing them, program products from a number of vendors can be used, including finite element analysis packages from ANSYS, Inc., of Canonsburg, PA, and SIMULIA(Abaqus) software products from Dassault Systémes of Waltham, MA.

Optionally, one or more arch or palate expander designs can be selected for testing or force modeling. As noted above, a desired tooth movement, as well as a force system required or desired for eliciting the desired tooth movement, can be identified. Using the simulation environment, a candidate arch or palate expander design can be analyzed or modeled for determination of an actual force system resulting from use of the candidate appliance. One or more modifications can optionally be made to a candidate appliance, and force modeling can be further analyzed as described, e.g., in order to iteratively determine an appliance design that produces the desired force system.

In block 1340, instructions for fabrication of the orthodontic appliance incorporating the arch or palate expander design are generated. The instructions can be configured to control a fabrication system or device in order to produce the orthodontic appliance with the specified arch or palate expander design. In some embodiments, the instructions are configured for manufacturing the orthodontic appliance using direct fabrication (e.g., stereolithography, selective laser sintering, fused deposition modeling, 3D printing, continuous direct fabrication, multi-material direct fabrication, etc.), in accordance with the various methods presented herein. In alternative embodiments, the instructions can be configured for indirect fabrication of the appliance, e.g., by thermoforming.

Method 1300 may comprise additional blocks: 1) The upper arch and palate of the patient is scanned intraorally to generate three dimensional data of the palate and upper arch; 2) The three dimensional shape profile of the appliance is determined to provide a gap and teeth engagement structures as described herein.

Although the above blocks show a method 1300 of designing an orthodontic appliance in accordance with some embodiments, a person of ordinary skill in the art will recognize some variations based on the teaching described herein. Some of the blocks may comprise sub-blocks. Some of the blocks may be repeated as often as desired. One or more blocks of the method 1300 may be performed with any suitable fabrication system or device, such as the embodiments described herein. Some of the blocks may be optional, and the order of the blocks can be varied as desired.

Figure 14:
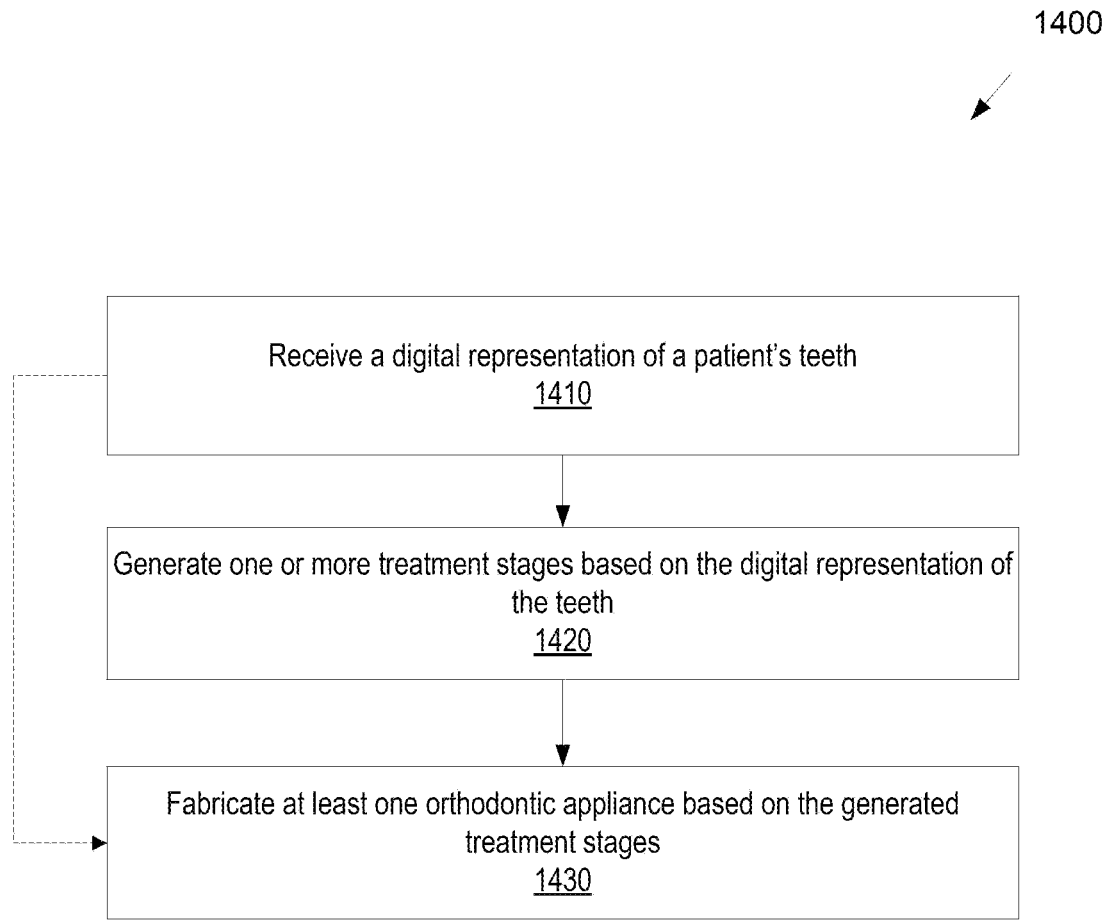
FIG. 14 illustrates a method for digitally planning an orthodontic treatment, in accordance with embodiments.

FIG. 14 illustrates a method 1400 for digitally planning an orthodontic treatment and/or design or fabrication of an appliance, in accordance with embodiments. The method 1400 can be applied to any of the treatment procedures described herein and can be performed by any suitable data processing system.

In block 1410, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.). The digital representation may be stored in a patient medical record in accordance with embodiments described herein.

In block 1420, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In block 1430, at least one orthodontic appliance is fabricated based on the generated treatment stages. For example, a set of appliances can be fabricated, each shaped according a tooth arrangement specified by one of the treatment stages, such that the appliances can be sequentially worn by the patient to incrementally reposition the teeth from the initial arrangement to the target arrangement. The appliance set may include one or more of the orthodontic appliances described herein. The fabrication of the appliance may involve creating a digital model of the appliance to be used as input to a computer-controlled fabrication system. The appliance can be formed using direct fabrication methods, indirect fabrication methods, or combinations thereof, as desired.

In some instances, staging of various arrangements or treatment stages may not be necessary for design and/or fabrication of an appliance. As illustrated by the dashed line in FIG. 14, design and/or fabrication of an orthodontic appliance, and perhaps a particular orthodontic treatment, may include use of a representation of the patient's teeth (e.g., receive a digital representation of the patient's teeth 1410), followed by design and/or fabrication of an orthodontic appliance based on a representation of the patient's teeth in the arrangement represented by the received representation.

In some implementations, fabrication instructions to fabricate a modified polymeric aligner based on the third digital model may be provided. In some implementations, the fabrication instructions may include: mold formation instructions to form a physical aligner mold for the polymeric aligner using the third digital model; and/or thermoforming instructions to thermoform the polymeric aligner from a sheet of polymeric material placed over the physical aligner mold. As noted herein, the third digital model may include one or more structural features at points relative to corresponding points of the second digital model, the one or more structural features being configured to accommodate the one or more corrective actions. In various implementations, the fabrication instructions comprise direct fabrication instructions to directly fabricate the polymeric aligner using the third digital model. As noted herein, the third digital model may include one or more areas of modified thickness relative to corresponding areas of the second digital model, the one or more areas of modified thickness being configured to accommodate the one or more corrective actions It is to be understood that the above description is intended to be illustrative, and not restrictive. Many other embodiments will be apparent upon reading and understanding the above description. Although embodiments of the present disclosure have been described with reference to specific example embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. A method of cryptographically secured digital dental treatment planning, comprising:
   generating, at an intraoral scanning system, a three-dimensional (3D) virtual model of a patient's dental arch based on stitching together a plurality of intraoral scans of the patient's dental arch, wherein the 3D virtual model comprises a 3D surface representing the patient's dentition at a first arrangement;
   encrypting, at the intraoral scanning system, the 3D virtual model using a secret cryptographic key to create a cryptographically secured dental record of the patient's dentition;
   adding data of the cryptographically secured dental record comprising the 3D virtual model to a blockchain;
   receiving, at a treatment planning system, the cryptographically secured dental record of the patient's dentition;
   decrypting, at the treatment planning system, the cryptographically secured dental record;
   determining, at the treatment planning system, a target arrangement for the patient's dentition;
   determining, at the treatment planning system, a digital treatment plan for the patient's dentition, wherein the digital treatment plan comprises a series of intermediate arrangements for a series of aligners to move the patient's dentition from the first arrangement toward the target arrangement;
   adding, at the treatment planning system, the digital treatment plan to the cryptographically secured dental record of the patient's dentition; and
   sending, from the treatment planning system, the cryptographically secured dental record of the patient's dentition to one or more data stores to store the cryptographically secured dental record of the patient's dentition.

2. The method of claim 1, further comprising:
   receiving the cryptographically secured dental record of the patient's dentition by a manufacturing system; and
   manufacturing the series of aligners by the manufacturing system using the cryptographically secured dental record.

3. The method of claim 2, wherein manufacturing the series of aligners comprises:
   causing one or more 3D printing machines to print a plurality of stereolithography (SLA) molds corresponding to the series of intermediate arrangements;
   causing one or more thermoforming machines to thermoform the series of aligners over the plurality of SLA molds; and
   causing one or more trimming machines to trim the series of aligners along a cutline.

4. The method of claim 2, wherein manufacturing the series of aligners comprises: causing one or more 3D printing machines to print the series of aligners.

5. The method of claim 1, wherein the 3D virtual model of the patient's dental arch is received at a first time, the method further comprising:
   generating, at the intraoral scanning system or at a second intraoral scanning system, and at a second time, a second 3D virtual model of the patient's dental arch, wherein the second 3D virtual model comprises a second 3D surface representing the patient's dentition at a second arrangement associated with a stage of orthodontic treatment;
   retrieving the cryptographically secured dental record of the patient's dentition; and
   adding the second 3D virtual model to the cryptographically secured dental record of the patient's dentition.

6. The method of claim 5, further comprising:
   determining a current arrangement of the patient's dentition based on the second 3D virtual model; and
   tracking progress of the digital treatment plan based on comparing the current arrangement of the patient's dentition to an intermediate arrangement of the patient's dentition from the digital treatment plan, wherein the intermediate arrangement of the patient's dentition is associated with a stage of treatment.

7. The method of claim 6, further comprising:
   determining that the current arrangement of the patient's dentition deviates from the intermediate arrangement of the patient's dentition;
   determining a revised digital treatment plan for the patient's dentition, wherein the revised digital treatment plan comprises a revised series of intermediate arrangements for a revised series of aligners to move the patient's dentition from the current arrangement toward the target arrangement; and adding the revised digital treatment plan to the cryptographically secured dental record of the patient's dentition.

8. The method of claim 1, further comprising:
digitally signing the cryptographically secured dental record by a node associated with the intraoral scanning system; and
digitally signing the cryptographically secured dental record by a node associated with the treatment planning system.

9. The method of claim 1, further comprising:
adding, to the blockchain, a transaction record associated with adding the digital treatment plan to the cryptographically secured dental record of the patient's dentition.

10. The method of claim 1, wherein the blockchain comprises a multi-dimensional blockchain comprising a main blockchain and one or more auxiliary blockchains.

11. The method of claim 10, wherein the one or more auxiliary blockchains store identifiers for locations of external storage storing the 3D virtual model.

12. A system comprising:
an intraoral scanning system configured to:
generate a three-dimensional (3D) virtual model of a patient's dental arch based on stitching together a plurality of intraoral scans of the patient's dental arch, wherein the 3D virtual model comprises a 3D surface representing the patient's dentition at a first arrangement;
encrypt the 3D virtual model using a secret cryptographic key to create a cryptographically secured dental record of the patient's dentition; and
add data of the cryptographically secured dental record comprising the 3D virtual model to a blockchain; and
a treatment planning system configured to:
receive the cryptographically secured dental record;
decrypt the cryptographically secured dental record;
determine a target arrangement for the patient's dentition;
determine a digital treatment plan for the patient's dentition, wherein the digital treatment plan comprises a series of intermediate arrangements for a series of aligners to move the patient's dentition from the first arrangement toward the target arrangement; and
add the digital treatment plan to the cryptographically secured dental record of the patient's dentition; and
a data store to store the cryptographically secured dental record of the patient's dentition.

13. The system of claim 12, further comprising:
a manufacturing system configured to:
receive the cryptographically secured dental record of the patient's dentition; and
manufacture the series of aligners using the cryptographically secured dental record.

14. The system of claim 13, wherein manufacturing the series of aligners comprises:
causing one or more 3D printing machines to print a plurality of stereolithography (SLA) molds corresponding to the series of intermediate arrangements;
causing one or more thermoforming machines to thermoform the series of aligners over the plurality of SLA molds; and
causing one or more trimming machines to trim the series of aligners along a cutline.

15. The system of claim 13, wherein manufacturing the series of aligners comprises:
causing one or more 3D printing machines to print the series of aligners.

16. The system of claim 12, wherein the 3D virtual model of the patient's dental arch is received at a first time, the system further comprising:
the intraoral scanning system or a second intraoral scanning system configured to:
generate, at a second time, a second 3D virtual model of the patient's dental arch, wherein the second 3D virtual model comprises a second 3D surface representing the patient's dentition at a second arrangement associated with a stage of orthodontic treatment;
retrieve the cryptographically secured dental record of the patient's dentition; and
add the second 3D virtual model to the cryptographically secured dental record of the patient's dentition.

17. The system of claim 16, wherein the treatment planning system, the intraoral scanning system, or the second intraoral scanning system is configured to:
determine a current arrangement of the patient's dentition based on the second 3D virtual model; and
track progress of the digital treatment plan based on comparing the current arrangement of the patient's dentition to an intermediate arrangement of the patient's dentition from the digital treatment plan, wherein the intermediate arrangement of the patient's dentition is associated with a stage of treatment.

18. The system of claim 17, wherein the treatment planning system, the intraoral scanning system, or the second intraoral scanning system is further configured to:
determine that the current arrangement of the patient's dentition deviates from the intermediate arrangement of the patient's dentition;
determine a revised digital treatment plan for the patient's dentition, wherein the revised digital treatment plan comprises a revised series of intermediate arrangements for a revised series of aligners to move the patient's dentition from the current arrangement toward the target arrangement; and
add the revised digital treatment plan to the cryptographically secured dental record of the patient's dentition.

19. The system of claim 12, wherein:
a node associated with the intraoral scanning system is configured to digitally sign the cryptographically secured dental record; and
a node associated with the treatment planning system is configured to digitally sign the cryptographically secured dental record.

20. The system of claim 12, wherein the treatment planning system is further configured to:
add, to the blockchain, a transaction record associated with adding the digital treatment plan to the cryptographically secured dental record of the patient's dentition.

* * * * *